US012667429B2

(12) United States Patent (10) Patent No.: US 12,667,429 B2
Park et al. (45) Date of Patent: Jun. 30, 2026

(54) METHOD FOR SYNCHRONIZING MOVEMENT CONTROL AND LOCATION RECOGNITION FOR MICRO-ROBOT BY USING BED-INTEGRATED ELECTROMAGNETIC FIELD APPARATUS

(71) Applicant: KOREA INSTITUTE OF MEDICAL MICROROBOTICS, Gwangju (KR)

(72) Inventors: Jong Oh Park, Gyeonggi-do (KR); Ja Young Kim, Daejeon (KR); Seong Hwan Jeong, Gwangju (KR)

(73) Assignee: KOREA INSTITUTE OF MEDICAL MICROROBOTICS, Gwangju (KR)

( * ) Notice: Subject to any disclaimer, the term of this patent is extended or adjusted under 35 U.S.C. 154(b) by 0 days.

(21) Appl. No.: 18/997,141

(22) PCT Filed: Jul. 20, 2023

(86) PCT No.: PCT/KR2023/010511
§ 371 (c)(1),
(2) Date: Jan. 20, 2025

(87) PCT Pub. No.: WO2024/025253
PCT Pub. Date: Feb. 1, 2024

(65) Prior Publication Data
US 2026/0026886 A1 Jan. 29, 2026

(30) Foreign Application Priority Data

Jul. 26, 2022 (KR) ........................ 10-2022-0092654

(51) Int. Cl.
A61B 34/20 (2016.01)
A61B 17/00 (2006.01)
(Continued)

(52) U.S. Cl.
CPC ........ A61B 34/20 (2016.02); A61B 17/00234 (2013.01); A61B 34/32 (2016.02);
(Continued)

(58) Field of Classification Search
CPC ......... A61B 34/20; A61B 34/32; A61B 90/37; A61B 17/00234; A61B 2034/2053;
(Continued)

(56) References Cited

U.S. PATENT DOCUMENTS

| | | | | |
|---|---|---|---|---|
| 2012/0149981 A1* | 6/2012 | Khait | ..................... | A61B 1/041 |
| | | | | 600/114 |
| 2019/0365486 A1* | 12/2019 | Srinivasan | ............. | A61B 34/30 |
| 2021/0341279 A1* | 11/2021 | Eskildsen | ............. | G01B 7/003 |

FOREIGN PATENT DOCUMENTS

| | | |
|---|---|---|
| KR | 10-2007-0041555 A | 4/2007 |
| KR | 10-2007-0086118 A | 8/2007 |

(Continued)

OTHER PUBLICATIONS

Liu, S., et al.; "Three-Dimensional Localization of a Robotic Capsule Endoscope Using Magnetoquasistatic Field", IEEE Access, vol. 8, 2020, pp. 141159-141169.

(Continued)

*Primary Examiner* — John D Li
(74) *Attorney, Agent, or Firm* — Harness, Dickey & Pierce, P.L.C.

(57) ABSTRACT

The present invention relates to a method for synchronizing movement control and location recognition for a micro-robot by using a bed-integrated electromagnetic field apparatus, and more specifically to a method for synchronizing movement control and location recognition for a micro-robot by using an electromagnetic field apparatus which enables precise movement control for a micro-robot and simultaneously enables location recognition for the micro- (Continued)

1000 robot, and enables miniaturization of the apparatus, thereby having excellent compatibility with other medical equipment.

7 Claims, 16 Drawing Sheets

(51) Int. Cl.
*A61B 34/32* (2016.01)
*A61B 90/00* (2016.01)

(52) U.S. Cl.
CPC .... *A61B 90/37* (2016.02); *A61B 2017/00345* (2013.01); *A61B 2034/2053* (2016.02); *A61B 2034/2065* (2016.02); *A61B 2090/376* (2016.02)

(58) Field of Classification Search
CPC ...... A61B 2034/2065; A61B 2090/376; A61B 2017/00345
See application file for complete search history.

(56) References Cited

FOREIGN PATENT DOCUMENTS

| | | | |
|---|---|---|---|
| KR | 10-2013-0024236 | A | 3/2013 |
| KR | 10-2019-0043778 | A | 4/2019 |
| KR | 10-2019-0135330 | A | 12/2019 |
| KR | 10-2022-0005878 | A | 1/2022 |

OTHER PUBLICATIONS

International Search Report from corresponding PCT Application No. PCT/KR2023/010511, dated Nov. 1, 2023.

* cited by examiner

METHOD FOR SYNCHRONIZING MOVEMENT CONTROL AND LOCATION RECOGNITION FOR MICRO-ROBOT BY USING BED-INTEGRATED ELECTROMAGNETIC FIELD APPARATUS

CROSS-REFERENCE TO RELATED APPLICATIONS

This application is a national phase application of PCT Application No. PCT/KR2023/010511, filed on Jul. 20, 2023, which claims the benefit and priority to Korean Patent Application No. 10-2022-0092654, filed on Jul. 26, 2022. The entire disclosures of the applications identified in this paragraph are incorporated herein by references.

TECHNICAL FIELD

This disclosure was made under the support of the Ministry of Health & Welfare, Republic of Korea under task identification number 1465041556 and task number RS-2023-00302153. The research management specialized institution of the said task is the Korea Health Industry Development Institute (KHIDI), the research project name is "Development of Medical Products Based on Microrobots", the research project name is "Development of an Active Guiding Catheter Medical Device for Coronary Intervention Procedures", the main institution is the Korea Micro Medical Robot Research Institute, and the research period is from Aug. 1, 2023 to Dec. 31, 2023.

The disclosure relates to a method of synchronizing movement control and location recognition of a micro-robot by using a bed-integrated electromagnetic field apparatus, and more specifically, to a method of synchronizing movement control and location recognition of a micro-robot by using an electromagnetic field apparatus which enables precise movement control of a micro-robot and simultaneously enables location recognition of the micro-robot in a human body, and enables miniaturization of the apparatus, thereby having excellent compatibility with other medical equipment.

BACKGROUND ART

Treatments using micro-robots, such as minimally invasive procedures, are being studied recently as surgical methods that can reduce patient pain and shorten recovery periods by enabling precise targeting of diseases and minimizing incision sites.

Methods of controlling the movement of micro-robots can be divided into external drive and self-driven methods. Self-driven methods include methods that use the pressure of gas generated by mutual chemical reactions between external fluid and the micro-robot body to propel the robot, and methods that use biological propulsion such as bacterial movement. However, self-driven methods have limitations in that they are difficult to apply to the human body due to low control freedom, low control precision, and chemical/biological toxicity issues for driving micro-robots.

The method of driving micro-robots by using magnetic fields is a representative external driving method with high safety in the human body and can be divided into methods using permanent magnets or electromagnetic driving coil apparatuses. Compared to the method using permanent magnets, the method of controlling micro-robots using electromagnetic driving coils has the advantage of being able to precisely control the strength and direction of the magnetic field by controlling the current applied to the coil, which makes it one of the most actively researched fields with a wide range of applications. Particularly, many studies are being conducted on propelling micro-robots or driving them for treatment using external magnetic fields, and most of the studies are being conducted on a two-dimensional plane or on simply moving in three-dimensional space. The electromagnetic driving coil apparatus is partially or entirely configured by a magnetic body so as to control medical apparatus by using magnetic fields without a battery or separate driver.

Medical apparatuses driven by electromagnets can be controlled using magnetic fields generated by applying current to coils fixedly placed externally. At this time, the desired driving of the medical apparatus can be implemented when the strength and direction of the current applied to each coil are controlled. The method using an electromagnet is easier to control than the method using a permanent magnet, and the movement of the medical apparatus can be quickly controlled according to the characteristics of the coil.

However, these existing driving apparatuses have many disadvantages in operating them due to the large number of electromagnets used. Specifically, since the existing electromagnetic field driving apparatuses use numerous electromagnets to drive the micro-robot, the size thereof increases, making them inefficient to install and operate in the treatment space, and due to the numerous electromagnets, the number of power supplies and required output increases, and power consumption is also very high. In addition, there were difficulties in using the apparatuses in compatibility with equipment used in other medical facilities, such as an X-ray device, due to limitations in the size of the existing electromagnetic field driving apparatus and the arrangement direction of the (electric) magnets.

In addition, conventional electromagnetic field driving apparatuses using permanent magnets generally control micro-robots by using two permanent magnets, but there is a difficulty in controlling the robot in a direction other than the direction in which the magnets are arranged, and although a control space for the permanent magnets is secured using a motor, there is a disadvantage in that real-time magnetic field control is difficult due to the time difference of the motor movement.

In order to recognize the location of a micro-robot, an image of an X-ray device has been used or a magnetic induction-based location recognition method has been designed. However, the X-ray-based location recognition method requires a process of rotating an X-ray device and taking images for multi-degree-of-freedom location recognition, and accordingly, it is difficult to obtain location information of the micro-robot in real time, and it is difficult to obtain information about the angle and bending shape of the micro-robot by using an X-ray image. In the magnetic induction-based location recognition method, three-axis coil arrangement is required in the micro-robot, the size of the micro-robot increases when mounted, and mounting itself is difficult on a hollow micro-robot. In addition, as with the X-ray-based location recognition method, obtaining information about the bending shape of the micro-robot is difficult. The location recognition method including individual apparatuses has the disadvantage of requiring separate technological development and apparatus configuration for the driving and location recognition of micro-robots.

Accordingly, there is an increasing need for an electromagnetic field driving apparatus and a method of synchronizing movement control and location recognition of a micro-robot by using the same, wherein precise movement control and location recognition of wired or wireless micro-robots can be simultaneously performed, and the apparatus can be miniaturized by minimizing the number of electro-magnets, thereby having excellent compatibility with medical equipment.

DISCLOSURE OF INVENTION

Technical Problem

The inventors have manufactured a bed-integrated electromagnetic field apparatus including a bed, a first electromagnet arranged in the bed, and second and third electromagnets arranged to form a predetermined angle with the first electromagnet, and have confirmed that the movement control and location recognition of a micro-robot may be performed simultaneously using the apparatus, and further, that when only the coordinates of a target lesion are input by a user, the micro-robot may be accurately targeted to the lesion site autonomously through location recognition information of the micro-robot acquired in real time and micro-robot drive utilizing the information.

The disclosure is to provide a method of synchronizing driving and location recognition of a micro-robot.

Also, the disclosure is to provide a micro-robot autonomous targeting method.

Also, the disclosure is to provide a computer program recorded in a computer-readable recording medium for executing a micro-robot autonomous targeting method.

Also, the disclosure is to provide a micro-robot autonomous targeting system including at least one processor for executing a micro-robot autonomous targeting method.

Solution to Problem

The disclosure relates to a method of synchronizing movement control and location recognition of a micro-robot by using a bed-integrated electromagnetic field apparatus, a method of autonomously targeting a micro-robot to a lesion by using the same, a computer program for executing the same, and a system.

The disclosure will be described in more detail below.

The term "human implantable medical apparatus" in this specification refers to all human implantable medical apparatuses that are partially or entirely surgically or medically designed and may be medical apparatuses inserted into the human body even after a procedure, to sustain life, or may include all medical apparatuses that may be temporarily inserted into the human body for a procedure or diagnosis. Particularly, in the disclosure, the human implantable medical apparatus includes a magnetic body that is magnetized in a magnetic field, and for example, a permanent magnet may be used as the magnetic body.

The term "micro-robot" as used herein refers to a type of human implantable medical apparatus, which may be classified into mechanical/electronic micro-robots including permanent magnets or soft magnets as millimeter-scale magnetic bodies, such as vascular robots and active capsule endoscopes, and polymer/cell-based micro-robots including magnetic nanoparticles as micro/nano-scale magnetic bodies, such as microcarriers for DDS, micro-scaffolds for cell therapy delivery, nanorobots, and macrophage robots, and may include other types of micro-robots.

An example of the disclosure relates to a bed-integrated electromagnetic field apparatus including a bed including a first electromagnet, and second and third electromagnets arranged to form a predetermined angle with the first electromagnet.

In the disclosure, the first electromagnet may be a coil in the form of a solenoid, a circle, a square, or a saddle.

In the disclosure, the first electromagnet may be in the form of a soft magnetic core or an air core.

The term "circular electromagnet" in this specification refers to a ring-shaped magnet, i.e., a magnet free from demagnetization effects at the ends.

In the disclosure, the first electromagnet may generate a magnetic field in the z-axis direction.

The term "z-axis" in this specification refers to an axis parallel to the central axis of the first electromagnet and perpendicular to the longitudinal direction of the bed.

In the disclosure, the second electromagnet may be a coil in the form of a solenoid, a circle, a square, or a saddle.

In the disclosure, the third electromagnet may be a solenoid, a circular, square, or saddle-shaped coil.

In the disclosure, the second electromagnet may be in the form of a soft magnetic core or an air core.

In the disclosure, the third electromagnet may be in the form of a soft magnetic core or an air core.

In the disclosure, the second electromagnet may generate a magnetic field in the x-axis and y-axis directions.

In the disclosure, the third electromagnet may generate a magnetic field in the x-axis and y-axis directions.

The term "x-axis" in this specification refers to an axis that is perpendicular to the central axis of the first electromagnet and parallel to the longitudinal direction of the bed.

The term "y-axis" in this specification refers to an axis that is perpendicular to the central axis of the first electromagnet, perpendicular to the longitudinal direction of the bed, and perpendicular to the x-axis and the z-axis at the same time.

In an embodiment of the disclosure, the first electromagnet may include a first support plate arranged on one side thereof, a second support plate disposed opposite to the first support plate, a center part configured to connect the first support plate and the second support plate through a connection part, and a first winding wound along the periphery of the center part.

The center part of the first electromagnet according to the disclosure may form a hollow space, but is not limited thereto.

The connection part according to the disclosure may connect the first support plate and the second support plate to the center part, and the second electromagnet and the third electromagnet may each be brought into contact with the first electromagnet to form a predetermined angle.

The connection part according to the disclosure may further include groove part for facilitating connection with the second electromagnet and the third electromagnet, but is not limited thereto.

In an embodiment of the disclosure, at least one of the first support plate, the second support plate, the connection part, or the center may be formed of at least one material selected from the group consisting of a Fe—Co alloy, aluminum, pure iron, iron nitride, electrical steel containing bismuth, and a combination thereof, but is not limited thereto.

In an embodiment of the disclosure, the first winding may include a conductive metal, for example, enamel, copper, or aluminum, but is not limited thereto.

In an embodiment of the disclosure, the second electromagnet may include a first core part, and the first core part may include a first lower side surface arranged to form a predetermined angle with the first electromagnet and a first upper side surface disposed opposite to the first lower side surface, and the second electromagnet may include a second winding wound between the first lower side surface and the first upper side surface.

In an embodiment of the disclosure, the third electromagnet may include a second core part, and the second core part may include a second lower side surface disposed to form a predetermined angle with the first electromagnet and a second upper side surface disposed opposite to the second lower side surface, and the third electromagnet may include a third winding wound between the second lower side surface and the second upper side surface.

In an embodiment of the disclosure, the first upper side surface may be disposed to face the central axis of the first electromagnet.

In an embodiment of the disclosure, the second upper side surface may be disposed to face the central axis of the first electromagnet.

In an embodiment of the disclosure, the second electromagnet and the third electromagnet may be disposed to face each other.

The first lower side surface of the second electromagnet according to the disclosure may be arranged to form an angle of 0 to 90 degrees, 0 to 80 degrees, 0 to 75 degrees, 0 to 70 degrees, 0 to 65 degrees, 0 to 50 degrees, 0 to 45 degrees, 0 to 40 degrees, 30 to 60 degrees, 30 to 50 degrees, or 35 to 45 degrees with the support plate of the first electromagnet or the connection part of the first electromagnet, and for example, may be arranged to form an angle of 0 to 45 degrees, but is not limited thereto.

The second lower side surface of the third electromagnet according to the disclosure may be arranged to form an angle of 0 to 90 degrees, 0 to 80 degrees, 0 to 75 degrees, 0 to 70 degrees, 0 to 65 degrees, 0 to 50 degrees, 0 to 45 degrees, 0 to 40 degrees, 30 to 60 degrees, 30 to 50 degrees, or 35 to 45 degrees with the support plate of the first electromagnet or the connection part of the first electromagnet, and for example, may be arranged to form an angle of 0 to 45 degrees, but is not limited thereto.

In an embodiment of the disclosure, the second winding may include a conductive metal, for example, enamel, copper or aluminum, but is not limited thereto.

In an embodiment of the disclosure, the third winding may include a conductive metal, for example, enamel, copper or aluminum, but is not limited thereto.

In an embodiment of the disclosure, the first core part may be formed of at least one material selected from the group consisting of a Fe—Co alloy, aluminum, pure iron, iron nitride, electrical steel containing bismuth, and a combination thereof, but is not limited thereto.

In an embodiment of the disclosure, the second core part may be formed of at least one material selected from the group consisting of a Fe—Co alloy, aluminum, pure iron, iron nitride, electrical steel containing bismuth, and a combination thereof, but is not limited thereto.

In an embodiment of the disclosure, the bed may include one or more bent parts, and a support part arranged between one or more bent parts.

In an embodiment of the disclosure, the curvature of the bent part may be formed in a shape corresponding to the angle at which the second coil is arranged.

In an embodiment of the disclosure, the first electromagnet, the second electromagnet, and the third electromagnet may be arranged inside the bed.

In an embodiment of the disclosure, the bed may further include a power supply part configured to supply power to the first electromagnet, the second electromagnet, and the third electromagnet.

In the disclosure, the power supply part may be arranged inside the bed.

In an embodiment of the disclosure, the bed may further include a moving part configured to linearly move the first electromagnet, the second electromagnet, and the third electromagnet.

In an embodiment of the disclosure, the bed may further include a cooling part configured to cool heat generated from the first electromagnet, the second electromagnet, the third electromagnet, the bed, the power supply part, or the moving part.

In the disclosure, the cooling part may be arranged inside the bed.

In an embodiment of the disclosure, the apparatus may further include a micro-robot including a magnetic body.

The micro-robot 300 according to the disclosure may be implemented as wired or wireless.

The micro-robot according to the disclosure may further include one or more components selected from the group consisting of a camera module, a location information providing part, a driving part, a treatment part, a robot controller, a data transmitting/receiving part, and a wireless power receiving part.

In an embodiment of the disclosure, the apparatus may include: a first electromagnet including a first support plate arranged on one side thereof, a second support plate disposed opposite to the first support plate, a center part configured to connect the first support plate and the second support plate through a connection part, and a first winding wound along the periphery of the center part; a second electromagnet including a first core part including a first lower side surface arranged to form a predetermined angle with the first support plate and a first upper side surface disposed opposite to the first lower side surface, and a second winding wound between the first lower side surface and the first upper side surface; a third electromagnet including a second core part including a second lower side surface arranged to form a predetermined angle with the first support plate and a second upper side surface disposed opposite to the second lower side surface, and a third winding wound between the second lower side surface and the second upper side surface; and a bed including one or more bent parts, and a support part disposed between the one or more bent parts, the bed having the first electromagnet, the second electromagnet, and the third electromagnet arranged therein.

Another example of the disclosure relates to a micro-robot driving method including an application operation of forming an electromagnetic field by applying a current to an electromagnetic field apparatus including a first electromagnet, a second electromagnet, and a third electromagnet.

Since the micro-robot driving method according to the disclosure includes the same configuration as the bed-integrated electromagnetic field apparatus described above, descriptions of common content therebetween are omitted to avoid excessive complexity of the specification.

In an embodiment of the disclosure, the application operation may further include an operation of applying currents of different directions to the first electromagnet, the second electromagnet, and the third electromagnet.

In an embodiment of the disclosure, the method may further include an adjustment operation of adjusting the location of the micro-robot by adjusting the magnitude or direction of the current to be applied to the first electromagnet, the second electromagnet, and the third electromagnet.

Another example of the disclosure relates to a method of synchronizing driving and location recognition of a micro-robot, the method including an image acquisition operation, a current application operation, a steering operation, and a location recognition operation.

In the disclosure, each operation included in the micro-robot driving and location recognition synchronization method may be performed by a data processing part included in the bed-integrated electromagnetic field apparatus of the disclosure or provided separately, but is not limited thereto.

In the disclosure, the data processing part may include at least one operation processing part configured to control the interpretation of digital instructions and the processing of data calculations, comparisons, etc., but is not limited thereto.

In the disclosure, the image acquisition operation may include acquiring an X-ray image of an Rx module by using an X-ray device.

In the disclosure, the direct current-alternating current (DC-AC) integrated current may be independently applied to the first electromagnet, the second electromagnet, and the third electromagnet included in the electromagnetic field apparatus.

In the disclosure, the steering operation may include driving the micro-robot by applying a DC current to the first electromagnet, the second electromagnet, and the third electromagnet.

In an embodiment of the disclosure, the micro-robot may be a catheter-type micro-robot.

In the disclosure, the location recognition operation may include recognizing the location of the micro-robot by using an alternating magnetic field generated by applying an alternating current to the first electromagnet, the second electromagnet, and the third electromagnet.

In a specific example of the disclosure, the location recognition operation may include a mixed signal receiving operation, a first extraction operation, a second extraction operation, an integration operation, and a conversion operation.

In the disclosure, the mixed signal receiving operation may include receiving a mixed signal generated from an Rx module included in a micro-robot by an AC magnetic field generated by applying an AC current to the first electromagnet, the second electromagnet, and the third electromagnet.

In the disclosure, the first extraction operation may include distinguishing and extracting a frequency-specific signal from the mixed signal.

In the disclosure, the second extraction operation may include extracting location estimation information of the Rx module from an X-ray image.

In the disclosure, the second extraction operation may be performed by extracting, from the X-ray image, an area where the Rx module is estimated to be located, by using an image processing technique used in medical imaging.

In the disclosure, the medical imaging may be at least one selected from the group consisting of an X-ray imaging, a magnetic resonance imaging (MRI), an ultrasound imaging, and a positron emission tomography (PET), and for example, may be an X-ray imaging, but is not limited thereto.

In the disclosure, the integration operation may include integrating a frequency-specific signal with the location estimation information having two degrees of freedom (2DoF), thereby generating first location information.

In the disclosure, the conversion operation may include generating second location information having five degrees of freedom (5DoF) from the first location information.

In the disclosure, the first extraction operation may be performed using a Fast Fourier Transform (FFT) algorithm, but is not limited thereto.

In the disclosure, the second extraction operation may include extracting location estimation information of the Rx module including x, y coordinate information of the Rx module from an X-ray image by labeling coordinates at which the Rx module is estimated to be located, but is not limited thereto.

In the disclosure, the integration operation may be performed by transmitting x, y coordinate information of the Rx module from an X-ray image to 5DoF Inverse model, but is not limited thereto.

In the disclosure, the Rx module may include at least one Rx coil, and may be two or more, three or more, four or more, or five or more coils, but is not limited thereto, and may include an appropriate number of Rx coils according to the length of the catheter-type micro-robot.

In a specific example of the disclosure, the Rx module may include three Rx coils, namely, a first Rx coil, a second Rx coil, and a third Rx coil.

In the disclosure, the one or more Rx coils may be spaced apart from each other by a predetermined interval.

In a specific example of the disclosure, the first Rx coil and the second Rx coil may be spaced apart by a predetermined interval.

In a specific example of the disclosure, the second Rx coil and the third Rx coil may be spaced apart by a predetermined interval.

In the disclosure, the conversion operation may be performed using 5DoF Inverse model, but is not limited thereto.

In a specific example of the disclosure, the conversion operation may further include a noise removal operation.

In a specific example of the disclosure, the noise removal operation may include removing noise of second location information by using a Kalman filter.

Another example of the disclosure relates to a micro-robot autonomous targeting method including a coordinate input operation, a target lesion information generation operation, a path generation operation, and a micro-robot driving and location recognition operation.

In the disclosure, each operation included in the micro-robot autonomous targeting method may be performed by a data processing part included in the bed-integrated electromagnetic field apparatus of the disclosure or provided separately, but is not limited thereto.

In the disclosure, the coordinate input operation may include receiving the coordinates of a target lesion from a user. Here, the coordinates may be three-dimensional coordinates, but are not limited thereto.

In the disclosure, the target lesion information generation operation may include generating location information of the lesion by using the coordinates of the target lesion input by the user.

In the disclosure, the path generation operation may include generating, by using the generated location information of the lesion, a three-dimensional movement path through which the micro-robot moves from the current location to the target lesion.

In the disclosure, the micro-robot driving and location recognition operation may include driving the micro-robot according to the movement path and recognizing the current location of the micro-robot in real time.

In a specific example of the disclosure, the micro-robot driving and location recognition operation may include an image acquisition operation, a current application operation, a steering operation, and a location recognition operation, similar to the method of synchronizing driving and location recognition of a micro-robot.

In the disclosure, the three-dimensional movement path may be a path for one end of the micro-robot to reach the coordinates of a target lesion. However, when new coordinates of the target lesion are received from the user in the path generation operation after generating the three-dimensional movement path, the path generation operation may include modifying the three-dimensional movement path. Accordingly, the micro-robot driving and location recognition operation may include driving the micro-robot according to the modified three-dimensional movement path and recognizing the current location.

Another example of the disclosure relates to a micro-robot autonomous targeting system including at least one processor for executing a micro-robot autonomous targeting method.

In the disclosure, the at least one processor of the micro-robot autonomous targeting system may receive coordinates of a target lesion, generate location information of the lesion by using the coordinates of the target lesion, generate, by using the location information of the lesion, a movement path through which the micro-robot moves from the current location to the target lesion, and drive the micro-robot according to the movement path and recognize the location of the micro-robot in real time.

In the disclosure, the processor may receive user operation information from a haptic device to drive the micro-robot.

In the disclosure, the processor may apply the location information generated by recognizing the location of the micro-robot in real time to a separate display apparatus, etc., and display the location of the micro-robot to the user in real time.

In the disclosure, the processor may generate, by using lesion location information input by the user, a movement path through which the micro-robot moves from the current location to the target lesion.

In the disclosure, the processor may drive the micro-robot according to the movement path and recognize the location of the micro-robot in real time.

In a specific example of the disclosure, the processor may drive the micro-robot in real time and recognize the location of the micro-robot by acquiring an X-ray image of an Rx module by using an X-ray device, apply a DC-AC integrated current independently to each of the first electromagnet, the second electromagnet, and the third electromagnet included in the bed-integrated electromagnetic field apparatus, drive the micro-robot by applying a DC current to the first electromagnet, the second electromagnet, and the third electromagnet, and recognize the location of the micro-robot by using the AC magnetic field generated by applying the AC current to the first electromagnet, the second electromagnet, and the third electromagnet. Through this, the processor may implement a control method (path-following) capable of following a targeting path.

In an embodiment of the disclosure, a computer program may configure a processing unit to operate as desired or may command the processing unit independently or collectively. The computer program may be permanently or temporarily embodied in any type of machine, component, physical apparatus, virtual equipment, computer storage medium, or apparatus in order to be analyzed by the processing unit or provide commands or data to the processing unit. Software may be distributed over networked computer systems and stored or executed in a distributed manner. The computer program may be stored on one or more computer-readable recording media.

The method of the disclosure may be implemented in the form of program commands that may be executed by various computer means, to be recorded in a computer-readable medium. The medium may continuously store a computer-executable program or temporarily store the same for execution or download. In addition, the medium may be a variety of recording means or storage means, either as a single unit or as a combination of multiple hardware components and may also be distributed over a network without being limited to a medium directly connected to a computer system. Examples of the medium may include magnetic media such as hard disks, floppy disks, and magnetic tapes, optical recording medium such as CD-ROMs and DVDs, magneto-optical medium such as floptical disks, and ROMs, RAMs, flash memories, etc. to be configured to store program instructions. In addition, examples of another medium may include recording medium or storage medium managed by App stores that distribute applications or other sites, servers, etc. that supply or distribute various software. The program commands recorded in the medium may be those specially designed and configured for the embodiments or may be known and available to those skilled in the art. Examples of program commands include not only machine language codes generated by a compiler, but also high-level language codes executable by a computer using an interpreter, etc.

Advantageous Effects of Invention

The disclosure relates to a method of synchronizing movement control and location recognition of a micro-robot by using a bed-integrated electromagnetic field apparatus, a method of autonomously targeting a micro-robot to a lesion by using the same, a computer program for executing the same, and a system thereof. According to the disclosure, the drive control and location recognition of a micro-robot can be performed simultaneously, thereby displaying the location of the micro-robot to a user in real time. Furthermore, when a user inputs only the coordinates of a target lesion, according to the disclosure, the micro-robot can be driven to the target lesion, and simultaneously, the location recognition of the micro-robot can be autonomously performed in real time.

BRIEF DESCRIPTION OF DRAWINGS

FIG. 11 is a flow chart showing a micro-robot driving-location recognition synchronization technology according to an embodiment of the disclosure.

FIG. 14 is a flow chart illustrating a micro-robot autonomous targeting technology utilizing for a micro-robot driving-location recognition synchronization technology according to an embodiment of the disclosure.

BEST MODE FOR CARRYING OUT THE INVENTION

Figure 1:
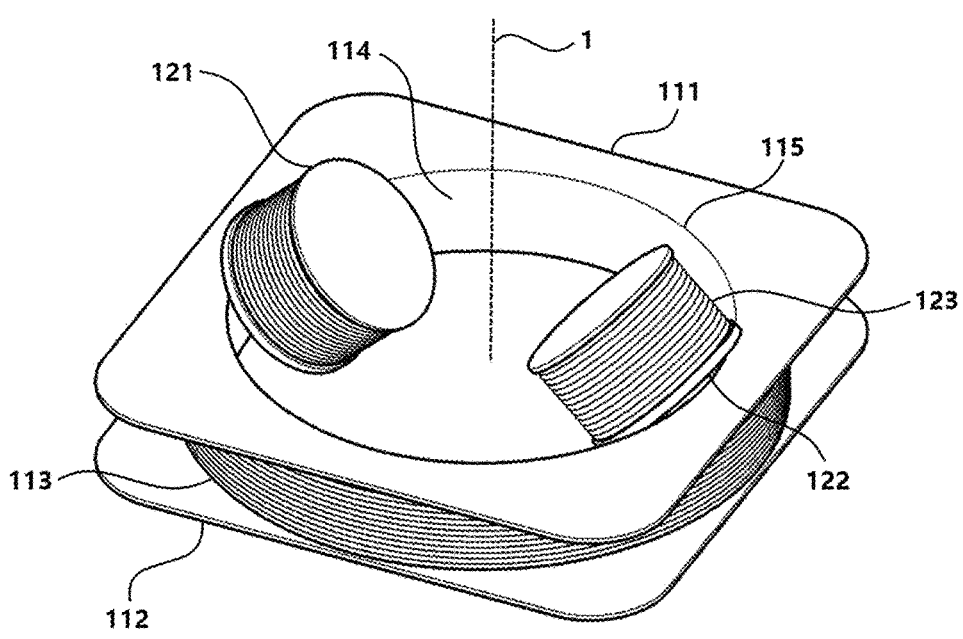
FIG. 1 illustrates an electromagnet module of a bed-integrated electromagnetic field apparatus according to an embodiment of the disclosure.

A method of synchronizing driving and location recognition of a micro-robot, including: an image acquisition operation of acquiring an X-ray image of an Rx module by using an X-ray device;

a current application operation of independently applying a DC-AC integrated current to each of a first electromagnet, a second electromagnet, and a third electromagnet included in the electromagnetic field apparatus;

a steering operation of driving a micro-robot by applying a DC current to the first electromagnet, the second electromagnet, and the third electromagnet; and a location recognition operation of recognizing the location of the micro-robot by using an AC magnetic field generated by applying an AC current to the first electromagnet, the second electromagnet, and the third electromagnet, wherein the location recognition operation includes:

a mixed signal reception operation of receiving a mixed signal generated from the Rx module included in the micro-robot by an AC magnetic field generated by applying an AC current to the first electromagnet, the second electromagnet, and the third electromagnet;

a first extraction operation of distinguishing and extracting a frequency-specific signal from the mixed signal;

a second extraction operation of extracting location estimation information of the Rx module from an X-ray image;

an integration operation of integrating the frequency-specific signal with the location estimation information having two degrees of freedom (2DoF), thereby generating first location information; and a conversion operation of generating second location information having five degrees of freedom (5DoF) from the first location information.

The above-described purpose, features, and advantages will become clearer through the detailed description below with reference to the attached drawings, so that those skilled in the art can easily practice the technical idea of the disclosure. In addition, when describing the disclosure, if it is determined that a detailed description of a known technology related to the disclosure may unnecessarily obscure the gist of the disclosure, the detailed description will be omitted.

Throughout the specification, when a part is said to "comprising or including" a certain component, this does not mean excluding other components, but rather includes other components, unless otherwise specifically stated. In addition, the term " . . . part" described in the specification means a unit that processes at least one function or operation, which may be implemented by hardware or software, or a combination of hardware and software. Furthermore, "a or an," "one," and similar related words may be used in the context of describing the disclosure to include both singular and plural meanings, unless otherwise indicated in the specification or clearly contradicted by the context.

In addition, when a component is said to be "linked" or "connected" to another component, it should be understood that it may be directly linked or connected to that other component, but there may be other components in between. On the other hand, when a component is said to be "directly linked" or "directly connected" to another component, it should be understood that there are no other components in between. Other expressions describing the relationship between components, such as "between" and "directly between" or "neighboring to" and "directly neighboring to", should be interpreted in the same way.

Figure 2:
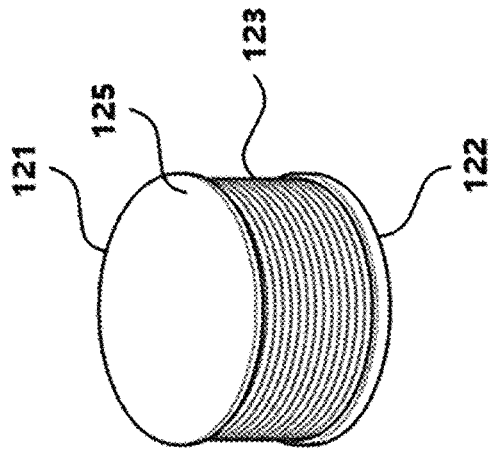
FIG. 2 illustrates a first electromagnet and a second electromagnet of a bed-integrated electromagnetic field apparatus according to an embodiment of the disclosure.
Figure 2:
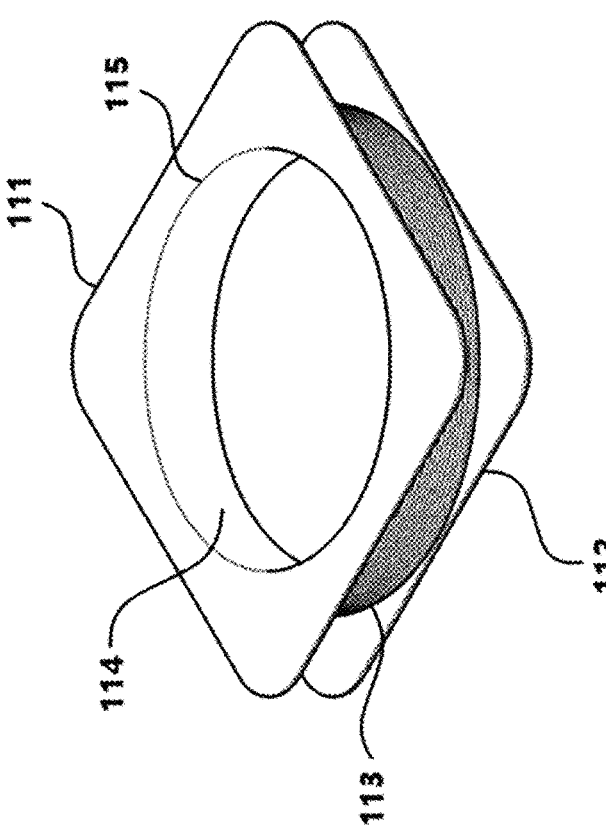
Figure 3:
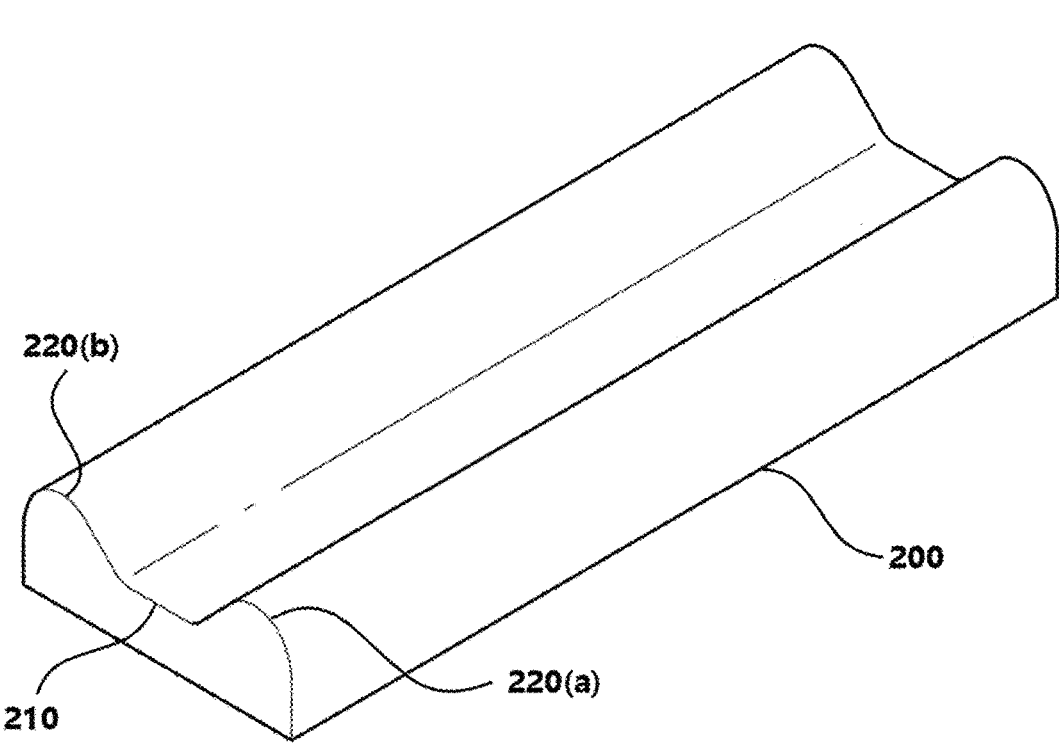
FIG. 3 illustrates a bed of a bed-integrated electromagnetic field apparatus according to an embodiment of the disclosure.
Figure 4:
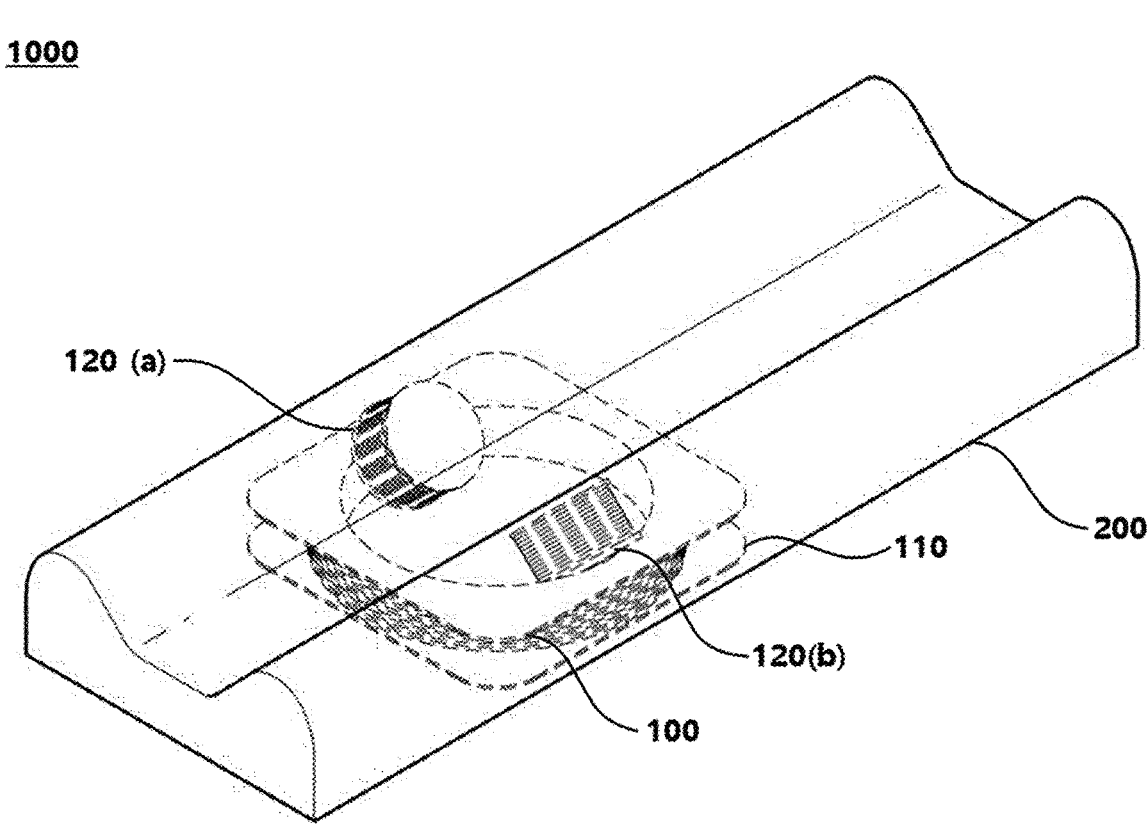
FIG. 4 is a perspective view of a bed-integrated electromagnetic field apparatus according to an embodiment of the disclosure.

FIG. 1 is a drawing showing an electromagnet module of a bed-integrated electromagnetic apparatus according to an embodiment of the disclosure, FIG. 2 is a drawing showing a first electromagnet and a second electromagnet (or a third electromagnet) of a bed-integrated electromagnetic apparatus according to an embodiment of the disclosure, FIG. 3 is a drawing showing a bed of a bed-integrated electromagnetic apparatus according to an embodiment of the disclosure, and FIG. 4 is a perspective view of a bed-integrated electromagnetic apparatus according to an embodiment of the disclosure.

Referring to FIGS. 1 to 4, a bed-integrated electromagnetic field apparatus 1000) according to one embodiment may include an electromagnet module 100 including a first electromagnet 110 and a second electromagnet 120(*a*) and a third electromagnet 120(*b*) arranged to form a predetermined angle with the first electromagnet 110, and a bed 200.

As illustrated in FIGS. 1 and 2, the first electromagnet 110 may be a circular electromagnet.

The first electromagnet 110 may include a first support plate 111 disposed on one side thereof, a second support plate 112 disposed on the other side of the first support plate 111, a center part 114 connecting the first support plate 111 and the second support plate 112 through a connection part 115, and a first winding 113 wound around the center part 114.

The first support plate 111 may be disposed on the upper side of the first electromagnet 110 and support the second electromagnet 120(a) and the third electromagnet 120(b) while being in contact with the second electromagnet 120(a) and the third electromagnet 120(b).

The first support plate 111 may include groove parts (not shown), and thus, may firmly support the second electromagnet 120(a) and the third electromagnet 120(b) when connected to the second electromagnet 120(a) and the third electromagnet 120(b).

The second support plate 112 may have a flat shape. The second support plate 112 may be disposed on the lower sides of the second electromagnet 120(a) and the third electromagnet 120(b) and support the entire electromagnet module 100 while being in contact with the lower side surface of the bed 200. In addition, even when the electromagnet module 100 is moved by the second support place 112, the first electromagnet 110, the second electromagnet 120(a), and the third electromagnet 120(b) may be firmly supported without change in the relative positions thereof.

The connection part 115 may connect the first support plate 111 and the second support plate 112 to the center part 114 and may be in the form of a corner of a vertically bent part as shown in FIGS. 1 to 4, but is not limited thereto, and may be in the form of a surface having a predetermined slope, for example.

The second electromagnet 120(a) and the third electromagnet 120(b) may be arranged on the first support plate 111 or the connection part 115 to form a predetermined angle. The connection part 115 may include grooves (not shown) that may be combined with the second electromagnet 120(a) and the third electromagnet 120(b), and at this time, the second electromagnet 120(a) and the third electromagnet 120(b) may be firmly attached to a predetermined position within the electromagnet module 100 by engaging with the grooves of the connection part 115.

The center part 114 may be connected to the first support plate 111 and the second support plate 112 through the connection part 115 and may be arranged to be perpendicular to the first support plate 111 and the second support plate 112.

The center part 114 may form hollow space in the first electromagnet 110 together with the first support plate 111, the second support plate 112, and the connection part 115. The first electromagnet 110 may form a space enabling the second electromagnet 120(a) and the third electromagnet 120(b) to be placed, through the hollow space formed at the center thereof, and accordingly, a part of the second electromagnet 120(a) and a part of the third electromagnet 120(b) may be placed within the hollow space while forming a predetermined angle with the first electromagnet 110.

The first electromagnet 110 may include the first winding 113 wound around the center part 114.

Current supplied from a bed-integrated electromagnetic field apparatus 1000 or a power supply part placed within the bed 200 may flow in the first winding 113, and since the center part 114 is placed in a direction perpendicular to the first support plate 111 and the second support plate 112, the first winding 113 may form an electromagnetic field in a direction perpendicular to the first support plate 111 and the second support plate 112.

Accordingly, the first electromagnet 110 may form an electromagnetic field in the upper and lower directions of the bed 200 when a current is applied to the first winding 113 wound around the center part 114, and through this, the location of a medical apparatus inserted into the human body may be adjusted up and down through a magnet embedded in a medical apparatus, for example, a micro-robot.

The first support plate 111, the second support plate 112, the connection part 115, and the center part 114 of the first electromagnet 110 may be formed of one or more materials selected from the group consisting of a Fe—Co alloy, aluminum, pure iron, iron nitride, electrical steel containing bismuth, and a combination thereof, but are not limited thereto.

The second electromagnet 120(a) and the third electromagnet 120(b) may be solenoid electromagnets, as illustrated in FIGS. 1 and 2.

The second electromagnet 120(a) may include a core part 125 including a lower side surface 122 arranged to form a predetermined angle with the first electromagnet 110 and an upper side surface 121 disposed opposite to the lower side surface 122, and a second winding 123 wound between the lower side surface 122 and the upper side surface 121.

The third electromagnet 120(b) may have the same structure as the second electromagnet 120(a) and may include a core part 125 including a lower side surface 122 arranged to form a predetermined angle with the first electromagnet 110 and an upper side surface 121 disposed opposite to the lower side surface 122, and a third winding 123 wound between the lower side surface 122 and the upper side surface 121.

The second electromagnet 120(a) and the third electromagnet 120(b) may be included in the bed-integrated electromagnetic field apparatus 1000 as illustrated in FIGS. 1 to 4.

The lower side surface 122 may be arranged to form a predetermined angle with the connection part 115 of the first electromagnet 110 or the first support plate 111, for example, may be arranged to form an angle of 0 to 45 degrees with the connection part 115 of the first electromagnet 110 or the first support plate 111, so that the strength and direction performance of the magnetic field in the longitudinal and width directions of the bed 200 may be optimized within the same allowable current, and the three-dimensional magnetic field control performance may be optimized together with the first electromagnet 100.

In addition, the lower side surface 122 may be firmly combined with the connection part 115 of the first electromagnet 110 or the first support plate 111 through a groove formed therein.

The second winding 123 may be wound between the lower side surface 122 and the upper side surface 121. In addition, the second winding 123 may include a conductive metal, for example, enamel, copper, or aluminum.

In addition, the third winding 123 may be wound between the lower side surface 122 and the upper side surface 121. In addition, the third winding 123 may include a conductive metal, for example, enamel, copper, or aluminum.

As illustrated in FIG. 1, the second electromagnet 120(a) and the third electromagnet 120(b) may be arranged obliquely with the first electromagnet 110 so as to form a predetermined angle with the first support plate 111 or the connection part 115 while a part of each of the second electromagnet 120(a) and the third electromagnet 120(b) is positioned in a hollow space formed in the first electromagnet 110. Accordingly, the second electromagnet 120(a) and the third electromagnet 120(b) may form electromagnetic fields in the forward, backward, left, and right directions of the bed-integrated electromagnetic field apparatus 1000.

In other words, as illustrated in FIG. 1, the second electromagnet may be arranged such that the upper side surface thereof 121 faces a central axis 1 of the first electromagnet 110, and accordingly, the human implantable medical apparatus may freely move in the x-axis and y-axis directions of the electromagnet module, as described later.

The bed 200 may include one or more bent parts 220(*a*), 220(*b*), and a support part 210 arranged between the one or more bent parts, and the electromagnet module 100 including the first electromagnet 110, the second electromagnet 120(*a*), and the third electromagnet 120(*b*) may be arranged inside the bed 200.

The support part 210 may have a flat shape to stably support the body of a patient.

The bed 200 may further include a power supply part configured to independently supply power to the first electromagnet 110, the second electromagnet 120(*a*), and the third electromagnet 120(*b*).

The bed 200 may further include a moving part (not shown) configured to linearly move the first electromagnet 110, the second electromagnet 120(*a*), and the third electromagnet 120(*b*).

The bed 200 may further include a cooling part configured to cool heat generated from the first electromagnet 110, the first electromagnet 110, the second electromagnet 120(*a*), the third electromagnet 120(*b*), the bed 130, the power supply part, or the moving part.

Figure 5:
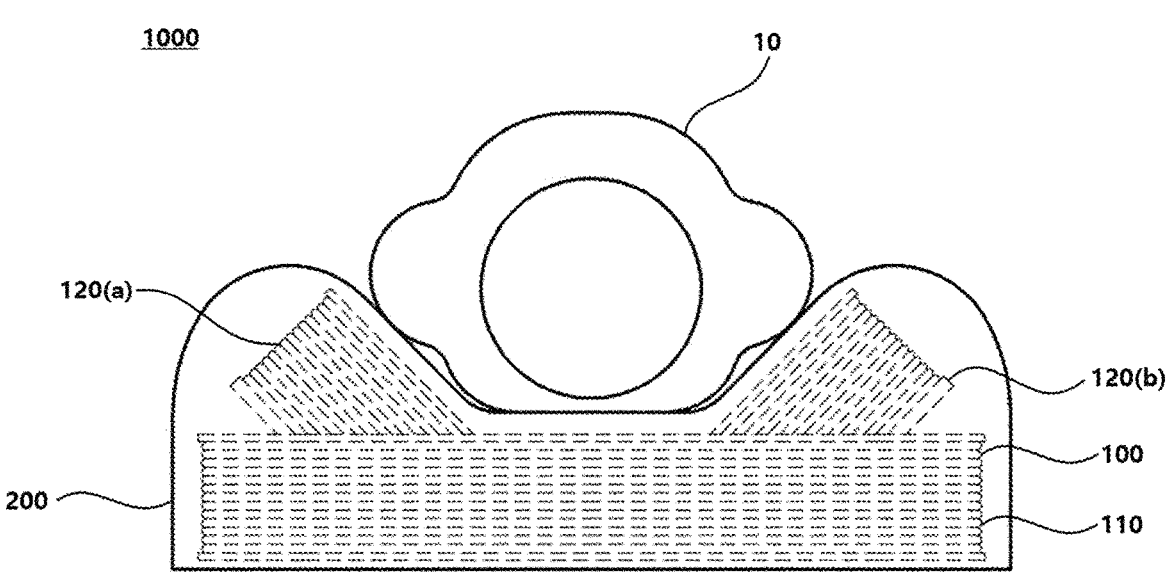
FIG. 5 is a side view of a bed-integrated electromagnetic field apparatus according to an embodiment of the disclosure.

Referring to FIG. 5, the curvature of the one or more of the bent parts 220(*a*), 220(*b*) may be formed in a shape corresponding to the angle at which the second electromagnet 120(*a*) and the third electromagnet 120(*b*) are arranged. Accordingly, the support part 210 and the bent parts 220(*a*), 220(*b*) of the bed 200 may be formed in a shape corresponding to the outer shape of the electromagnet module 100, thereby allowing the distance between the third electromagnet 120(*b*) and the body 10 of a patient positioned on the bed 200 and each of the first electromagnet 110, the second electromagnet 120(*a*), and to become even shorter.

That is, the distance between the medical apparatus inserted into the body of the patient and each of the first electromagnet 110, the second electromagnet 120(*a*), and the third electromagnet 120(*b*) is significantly reduced through the shape of the bed 200 corresponding to the electromagnetic module 100, so that the amount of current required for the electromagnet to move the human-implantable medical apparatus may be reduced, enabling the medical apparatus to be driven without consuming much power.

Figure 6:
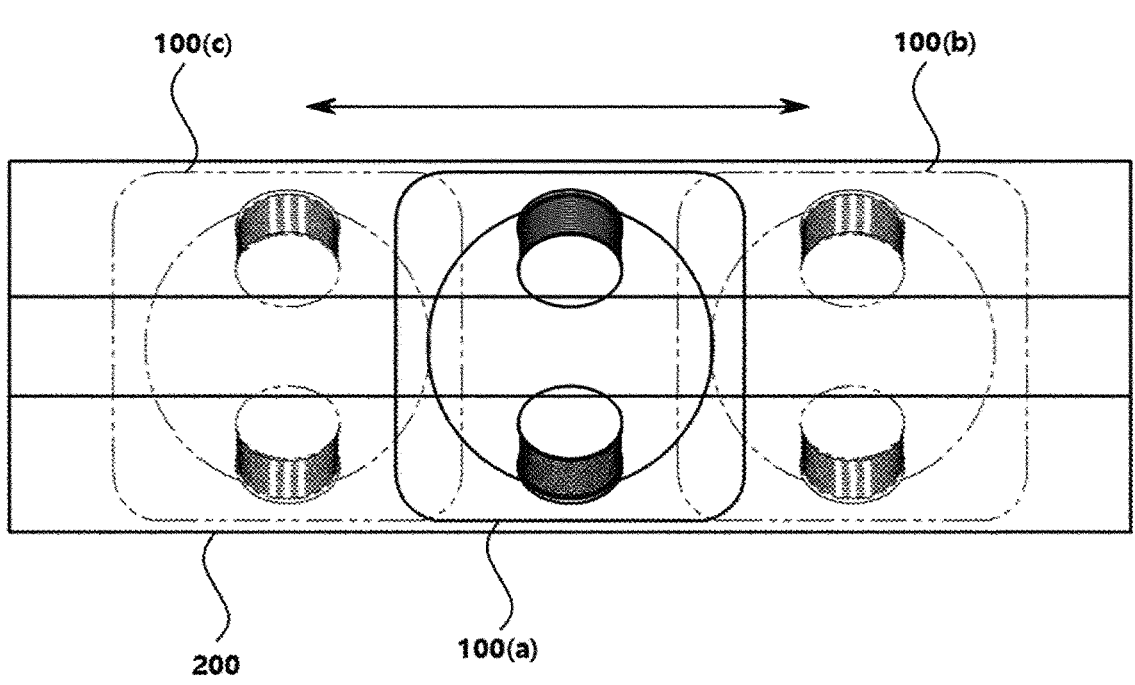
FIG. 6 illustrates linear movement of an electromagnet module in a bed-integrated electromagnetic field apparatus according to an embodiment of the disclosure.

FIG. 6 illustrates the linear movement of an electromagnet module in a bed-integrated electromagnetic field apparatus according to an embodiment of the disclosure.

Referring to FIG. 6, the electromagnet module 100 may linearly move to location 100(*a*), 100(*b*), 100(*c*) of the bed through the motor drive of the moving part (not shown) included in the bed 200 or the electromagnetic field apparatus 1000.

That is, according to an embodiment, the bed-integrated electromagnetic field apparatus 1000 may move the electromagnet module 100 to the location in the body of a patient positioned on the bed 200 where a disease is present or suspected, and as the electromagnet module 100 guides the medical apparatus to the location, the human body-implantable medical apparatus may be moved to the location.

Therefore, the bed-integrated electromagnetic field apparatus 1000 according to an embodiment may freely control the location of the inserted medical apparatus in the body of a patient through the linear movement of the electromagnet module 100.

Figure 7A:
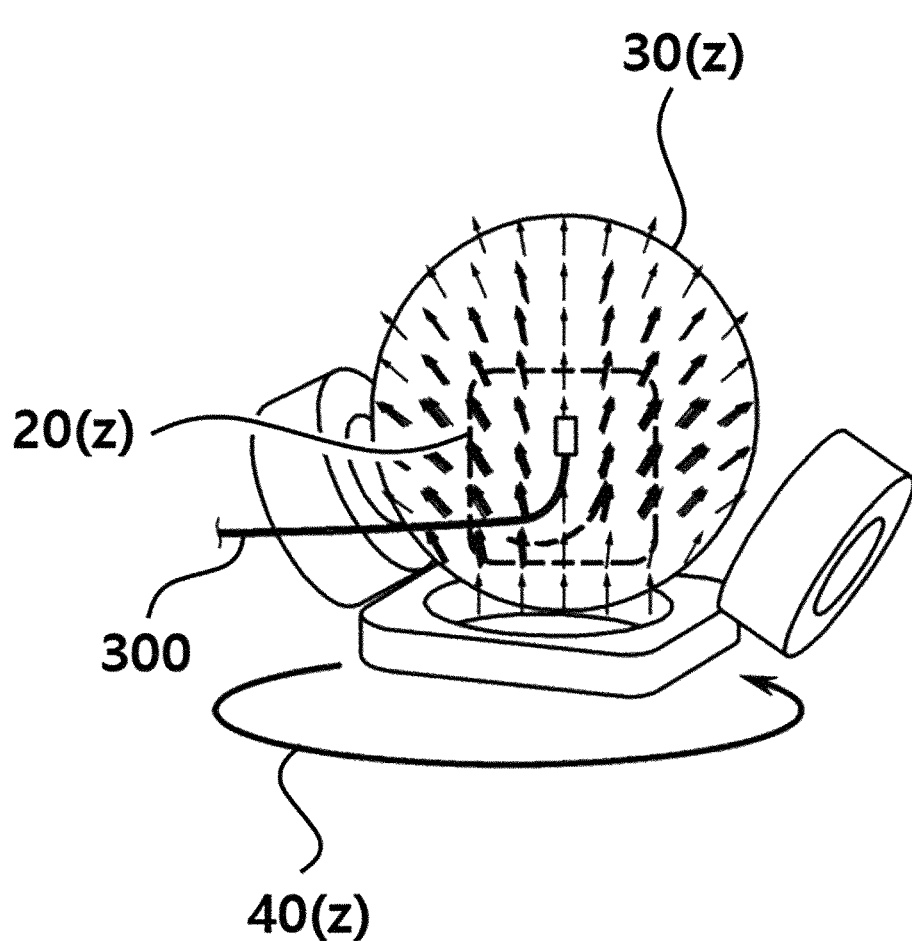
FIG. 7A illustrates forming an electromagnetic field in the z-axis direction of a bed-integrated electromagnetic field apparatus according to an embodiment of the disclosure.
Figure 7B:
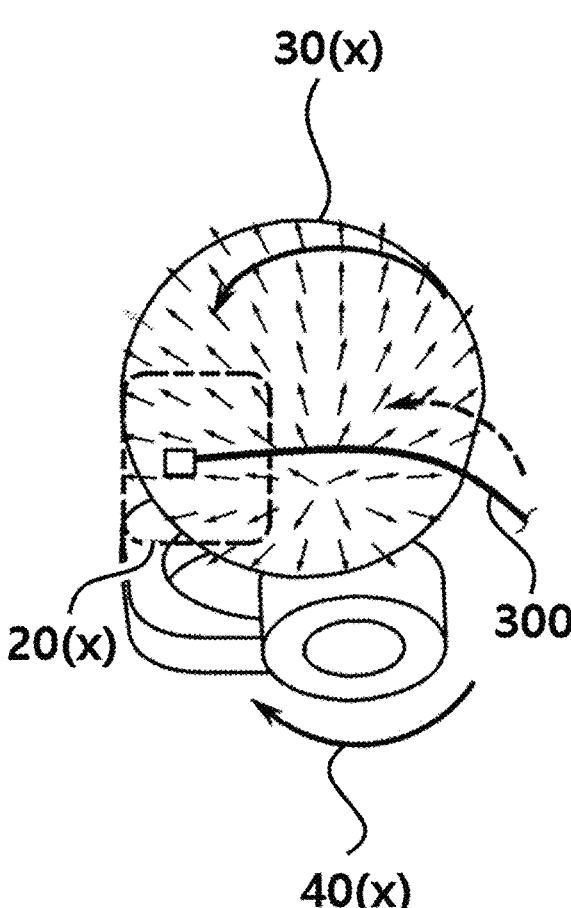
FIG. 7B illustrates forming an electromagnetic field in the x-axis direction of a bed-integrated electromagnetic field apparatus according to an embodiment of the disclosure.
Figure 7C:
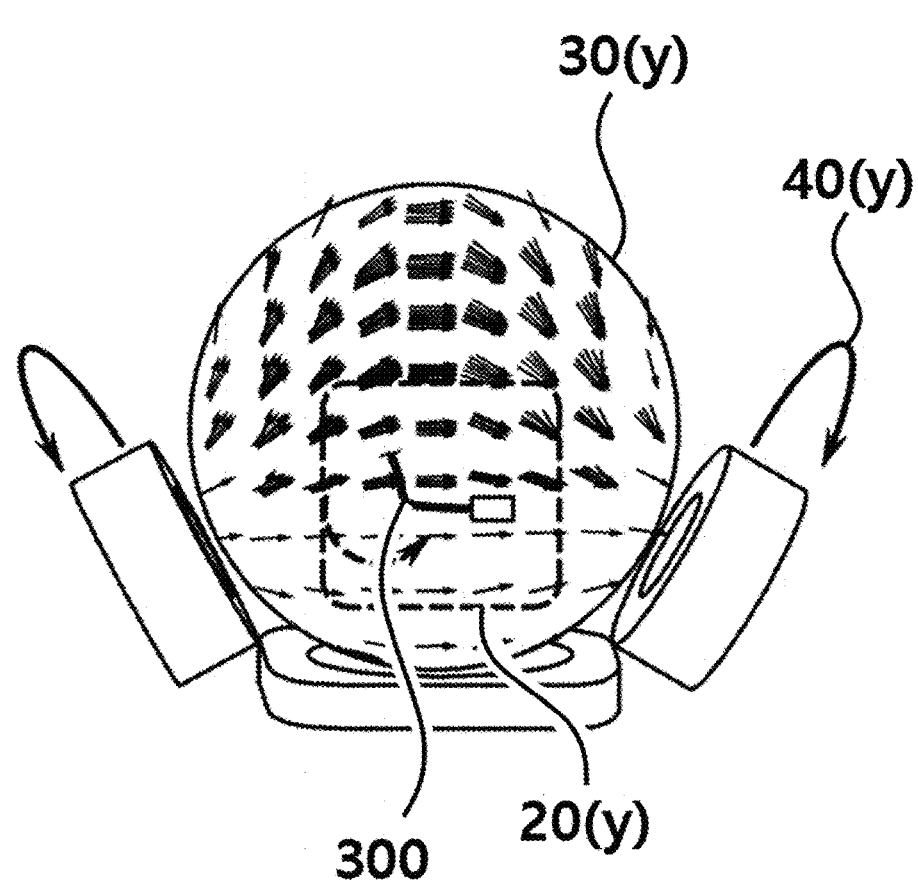
FIG. 7C illustrates forming an electromagnetic field in the y-axis direction of a bed-integrated electromagnetic field apparatus according to an embodiment of the disclosure.

FIG. 7A illustrates forming an electromagnetic field in the z-axis direction of a bed-integrated electromagnetic field apparatus according to an embodiment of the disclosure, FIG. 7B illustrates forming an electromagnetic field in the x-axis direction of a bed-integrated electromagnetic field apparatus according to an embodiment of the disclosure, and FIG. 7C illustrates forming an electromagnetic field in the y-axis direction of a bed-integrated electromagnetic field apparatus according to an embodiment of the disclosure.

Referring to FIGS. 7A to 7C, the bed-integrated electromagnetic field apparatus according to an embodiment may focus a magnetic field by using the first electromagnet, the second electromagnet, and the third electromagnet to move a micro-robot 300 to the region of interest.

Specifically, as illustrated in FIG. 7A, a user may move the micro-robot 300 in the z-axis direction by applying a current to the first electromagnet. At this time, the user may freely move the micro-robot 300 in the z-axis direction of the region of interest 20(*z*) by adjusting the direction and intensity 40(*z*) of the current to be applied to the first electromagnet, and accordingly, the user may appropriately drive the micro-robot 300 in the z-axis direction in the region of interest 20(*z*) in the body of a patient.

As illustrated in FIGS. 7B and 7C, the user may move the micro-robot 300 in the x-axis and y-axis directions by applying a current to the second electromagnet and the third electromagnet. As described above, the upper side surface of each of the second electromagnet and the third electromagnet may be arranged to face the central axis of the first electromagnet, and the lower side surface of each of the second electromagnet and the third electromagnet may be arranged to form a predetermined angle with the first support plate or connection part of the first electromagnet. Thus, the second electromagnet and the third electromagnet may move the micro-robot 300 in the x-axis and y-axis directions of the electromagnet module. In addition, similarly to the movement in the z-axis direction, the movement of the micro-robot 300 in the x-axis and y-axis directions may be achieved when the user adjusts the direction and intensity 40(*x*), 40(*y*) of the current to be applied to the second electromagnet and the third electromagnet to move the micro-robot 300 in the x-axis and y-axis directions, thereby freely moving the micro-robot 300 within the region of interest 20(*x*), 20(*y*).

At this time, the user may apply currents in opposite directions to the second electromagnet and the third electromagnet, thereby focusing the magnetic field and increasing the intensity of the magnetic field 30(*x*), 30(*y*) formed in the region of interest.

In summary, the user may adjust the direction and intensity of the current to be applied to the first electromagnet, the second electromagnet, and the third electromagnet to overlap the magnetic fields 30(*x*), 30(*y*), 30(*z*) generated by the first electromagnet and the second electromagnet on the region of interest 20(*x*), 20(*y*) 20(*z*) inside the body of a patient, thereby freely and precisely moving the micro-robot in the region of interest. That is, the micro-robot 300 may be precisely driven by independently adjusting the specific arrangement of the first and second electromagnets and the direction and intensity of the current applied to each electromagnet.

Figure 8:
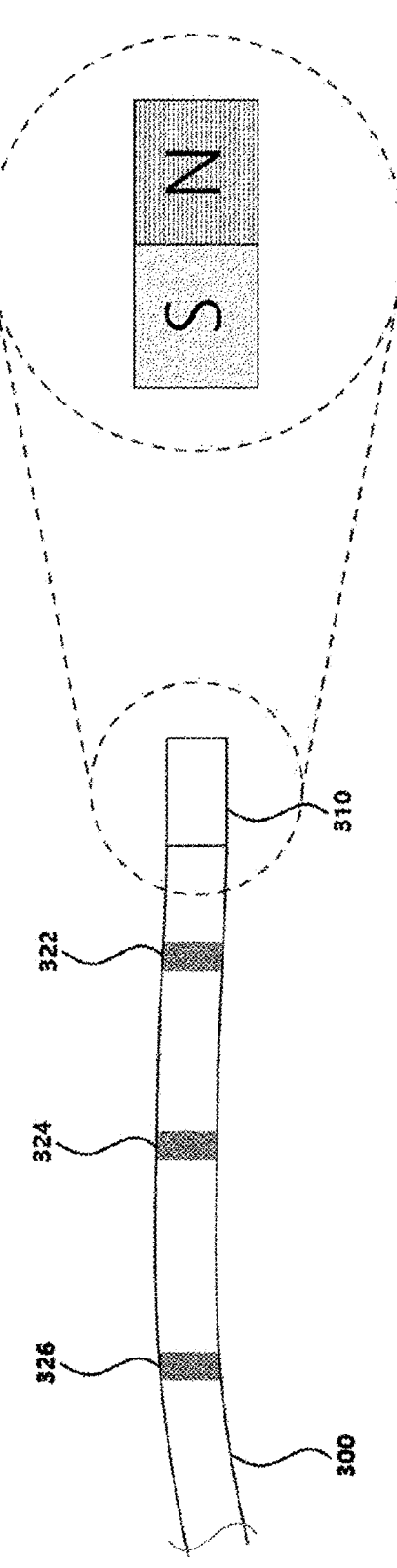
FIG. 8 illustrates a micro-robot of a bed-integrated electromagnetic field apparatus according to an embodiment of the disclosure.

FIG. 8 illustrates a micro-robot of a bed-integrated electromagnetic field apparatus according to an embodiment of the disclosure.

Referring to FIG. 8, the micro-robot 300 may include a magnet to have a magnetization direction. In addition, the micro-robot 300 may be rotated and/or moved in an arbitrary direction by a magnetic field generated by the bed-integrated electromagnetic field apparatus described above.

The micro-robot 300 may be implemented as wired or wireless.

The micro-robot 300 may include a robot body. The micro-robot 300 may include only the robot body 310 and may further include one or more components selected from a group consisting of a camera module, a location information providing part, a driving part, a treatment part, a robot controller, a data transmitting/receiving part, and a wireless power receiving part.

The robot body 310, which is part for defining the exterior of the micro-robot 300, may be manufactured to a size that allows movement inside a subject or inside a blood vessel. In addition, the front part of the robot body 310 may be manufactured in a streamlined shape so as to have less friction with blood flow, and the front part of the robot body 310 may be provided with a debris collector, etc., for collecting treatment fragments generated during vascular treatment.

Figure 9:
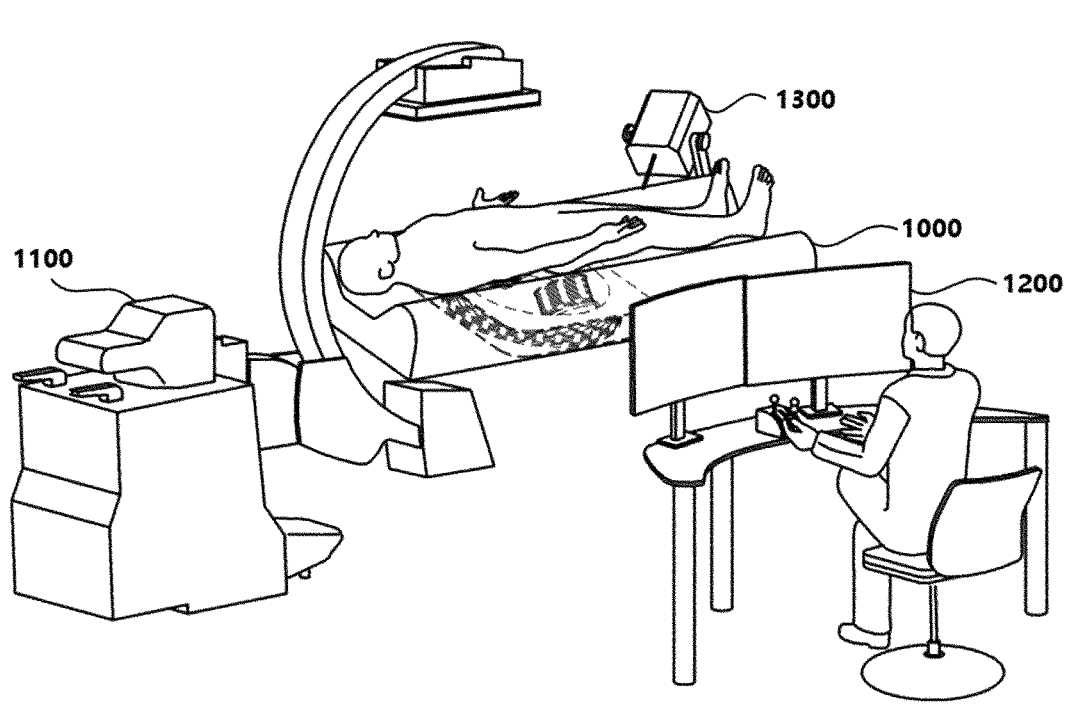
FIG. 9 illustrates a bed-integrated electromagnetic field apparatus being used in conjunction with a medical apparatus such as an X-ray device, according to an embodiment of the disclosure.

FIG. 9 illustrates a bed-integrated electromagnetic field apparatus being used in conjunction with a medical apparatus such as an X-ray device, according to an embodiment of the disclosure.

Referring to FIG. 9, the bed-integrated electromagnetic field apparatus 1000 according to an embodiment may be used in conjunction with an X-ray device 1100, an image navigation system 1200, and a catheter insertion-retrieval apparatus 1300 in a hospital.

Figure 10:
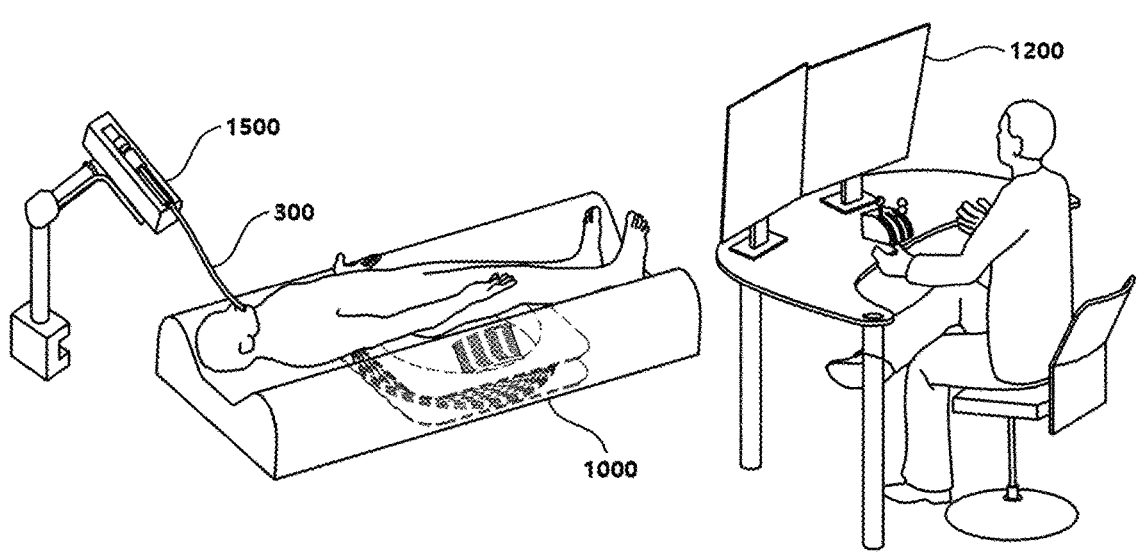
FIG. 10 illustrates a bed-integrated electromagnetic field apparatus being used in conjunction with a medical apparatus, such as a micro-robot guidance apparatus, according to an embodiment of the disclosure.

FIG. 10 illustrates a bed-integrated electromagnetic field apparatus being used in conjunction with a medical apparatus, such as a micro-robot guidance apparatus, according to an embodiment of the disclosure.

Referring to FIG. 10, a bed-integrated electromagnetic field apparatus 1000 according to an embodiment may be used in conjunction with a micro-robot guidance apparatus 1500 and an image navigation system 1200 in a hospital.

Therefore, the bed-integrated electromagnetic field apparatus 1000 may be implemented together with the micro-robot 300 as a vascular robot together with the catheter insertion-retrieval apparatus 1300 as illustrated in FIG. 9 or may be implemented together with the micro-robot 300 as a gastrointestinal endoscope together with the micro-robot guidance apparatus 1500 as illustrated in FIG. 10.

As described above, the bed-integrated electromagnetic field apparatus 1000 according to an embodiment has a minimized number of coils included in the apparatus, and has a structure integrated with the bed on which the body of a patient is positioned, enabling the size of the entire system to be miniaturized.

Accordingly, the compatibility with existing medical equipment is excellent, installation in a hospital is easy, and interference with the procedure operation due to the electromagnetic field system does not occur, making the procedure easy.

Figure 11:
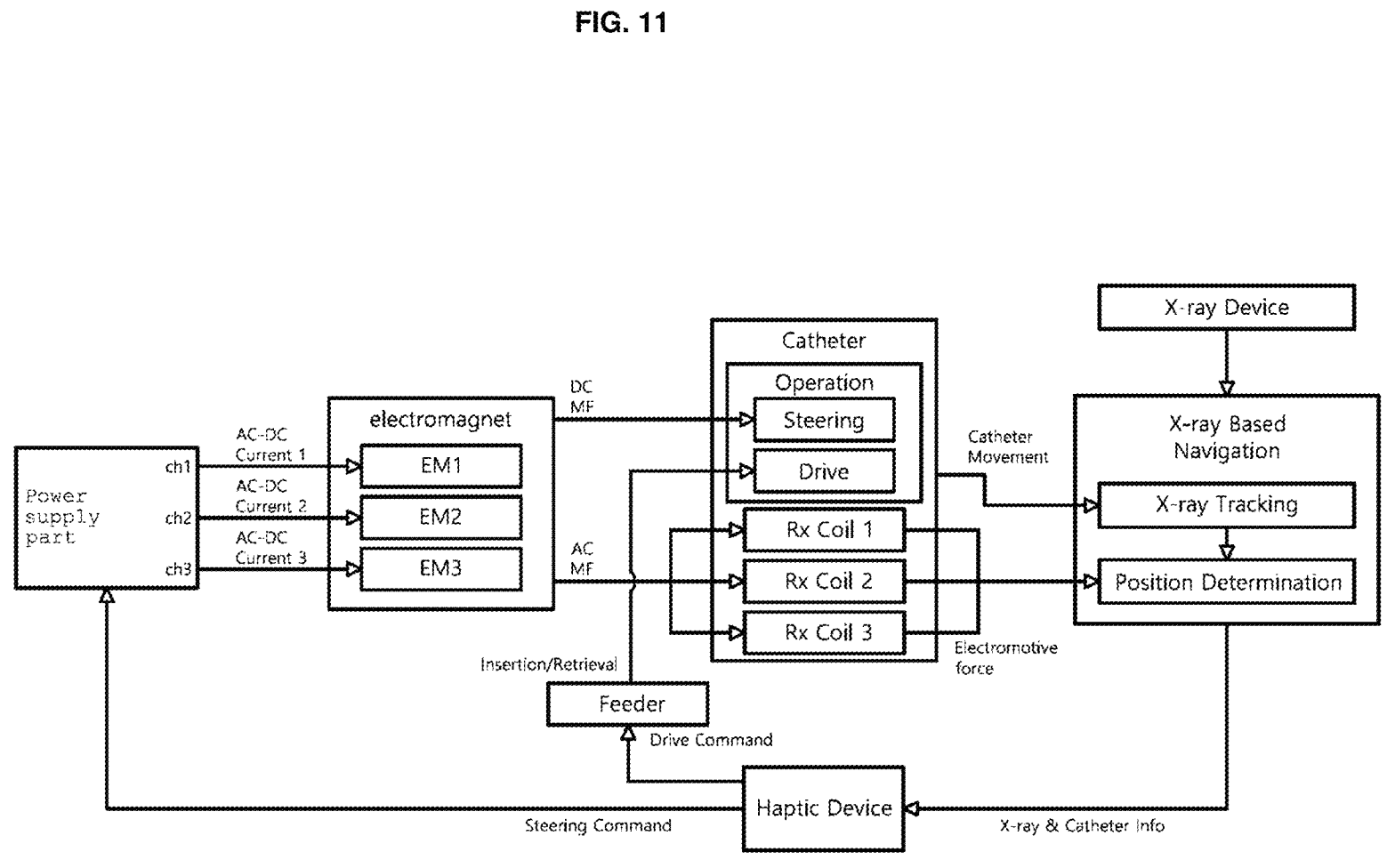

FIG. 11 is a flow chart showing a micro-robot driving-location recognition synchronization technology according to an embodiment of the disclosure.

Referring to FIG. 11, the micro-robot driving-location recognition synchronization method of the disclosure may include an image acquisition operation (S100) of acquiring an X-ray image of an Rx module by using an X-ray device, a current application operation (S200) of independently applying a DC-AC integrated current to each of the first electromagnet, the second electromagnet, and the third electromagnet included in the bed-integrated electromagnetic field apparatus, a steering operation (S300) of driving the micro-robot by applying the DC current to the first electromagnet, the second electromagnet, and the third electromagnet, and a location recognition operation (S400) of recognizing the location of the micro-robot by using an AC magnetic field generated by applying the AC current to the first electromagnet, the second electromagnet, and the third electromagnet.

The image acquisition operation (S100) may include acquiring an X-ray image of the Rx module by using an X-ray device. The image acquisition operation (S100) may be performed before the current application operation (S200) described below, but is not limited thereto, and may be performed in real time or at regular time intervals throughout the entire process in which the method of the disclosure is performed.

The current application operation (S200) may include independently applying an integrated current of direct current (DC) and alternating current (AC) to each of the first electromagnet 110 (EM1), the second electromagnet 120(*a*) (EM2), and the third electromagnet 120(*b*) (EM3) through a first channel (ch1), a second channel (ch2), and a third channel (ch3) of the power supply part, thereby generating a DC-AC integrated magnetic field.

In a DC-AC integrated magnetic field, the DC magnetic field may react with a magnetic body located at the end of a body 310 of the wired catheter-type micro-robot 300 to induce a steering motion of the micro-robot (S300), and reacting an AC magnetic field with the first to third Rx modules 322, 324, 326 (Rx Coils 1 to 3) of the micro-robot to induce an electromotive force (EMF) (S400).

Here, the location recognition operation (S400) may include a mixed signal receiving operation (S410) of receiving a mixed signal generated from an Rx module included in the micro-robot; a first extraction operation (S420) of distinguishing and extracting a frequency-specific signal from the mixed signal; a second extraction operation (S430) of extracting location estimation information of the Rx module from an X-ray image; an integration operation (S440) of generating first location information by integrating the frequency-specific signal with the location estimation information having two degrees of freedom (2DoF); and a conversion operation (S450) of generating, from the first location information, second location information having five degrees of freedom (5DoF).

The mixed signal receiving operation (S410) may include receiving a mixed signal generated from the first to third Rx modules 322, 324, 326 included in the micro-robot by using an AC magnetic field generated by applying an AC current to the first electromagnet, the second electromagnet, and the third electromagnet. The mixed signal receiving operation (S410) may be performed using a data acquisition part (not shown), and the data acquisition part may refer to an apparatus that is separately provided to receive a wireless signal or is provided in the bed-integrated electromagnetic field apparatus of the disclosure.

The first extraction operation (S420) may include distinguishing and extracting a frequency-specific signal from the mixed signal, the second extraction operation (S430) may include extracting location estimation information of the Rx module from an X-ray image, the integration operation (S440) may include integrating the frequency-specific signal with the location estimation information having two degrees of freedom (2DoF), thereby generating first location information, and the conversion operation (S450) may include generating, from the first location information, second location information having five degrees of freedom (5DoF).

The driving of the micro-robot by the steering operation (S300) may be implemented through insertion/retrieval operation using a feeder and steering using a direct current magnetic field. The process of recognizing the location of the micro-robot through the location recognition operation (S400) may be performed by transmitting the electromotive force information of the micro-robot to the image navigation system 1200 through wired communication and integrating the electromotive force information with the X-ray location estimation information of the micro-robot's distal end, generated using an X-ray image, thereby converting the electromotive force information into the bending shape information and the distal location of the micro-robot's five degrees of freedom (DoF) (5DoF; x, y, z, pitch, yaw).

When a micro-robot inserted into a human body is photographed using an X-ray, a material with high permeability is displayed in white-based colors in a black and white image, and a material with low permeability is displayed in black-based colors in the black and white image. In an X-ray image, the Rx coil part and magnet part constituting the micro-robot of the disclosure appear in black-based colors, whereas the catheter tube part of the micro-robot appears in a white color and thus is not easily visible due to the high X-ray permeability thereof. The location of the micro-robot may be estimated using image tracking technology, and X-ray location estimation information may be generated accordingly.

The location recognition operation (S400) may specifically include a mixed signal receiving operation (S410), a first extraction operation (S420) for extracting frequency-specific signals from the mixed signal, a second extraction operation (S430) for distinguishing and extracting location estimation information of the Rx module from a X-ray image, an integration operation (S440) for generating first location information by integrating the frequency-specific signal with the location estimation information, and a conversion operation (S450) for generating second location information from the first location information.

A user may manually configure the next movement path of the micro-robot by operating a haptic device after identifying the location information of the micro-robot shown in the X-ray image and the second location information through a separate display apparatus, etc. The operation information generated by the haptic device is transmitted to a feeder and the power supply part. The direct current (AC) may be changed in real time according to the operation of the haptic device. However, the alternating current (AC) is fixedly applied to the first electromagnet, the second electromagnet, and the third electromagnet with a frequency and magnitude configured for location recognition. The current application operation (S200) may be performed again after the location recognition operation (S400) and may also be performed simultaneously with the location recognition operation.

The location recognition operation (S400) as described above may be executable by a computer program or software recorded in a computer-readable recording medium. Each detailed operation included in the location recognition operation may be performed by at least one processor implemented to execute a computer-readable command.

Figure 12:
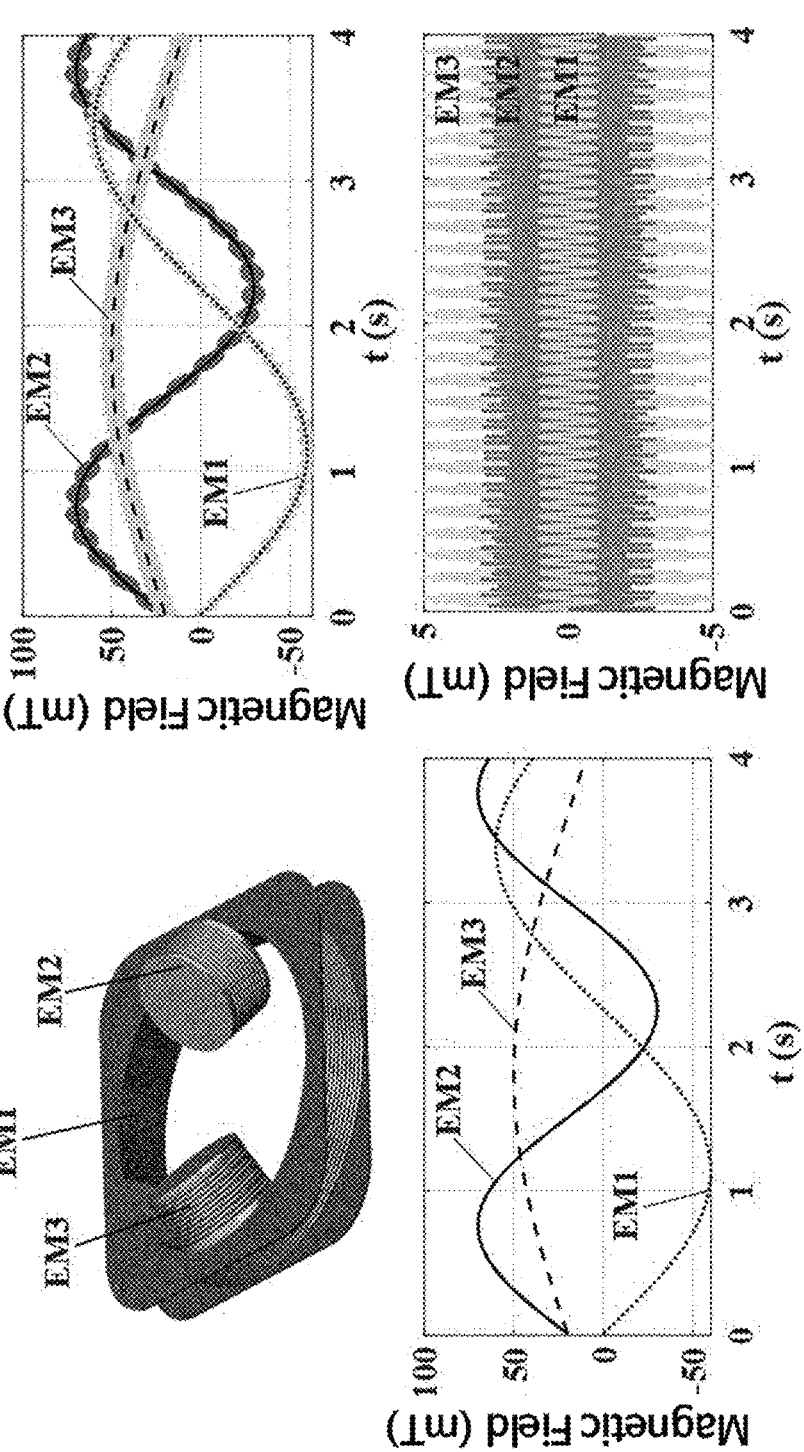
FIG. 12 illustrates a direct current (DC)-alternating current (AC) integrated magnetic field generated by a first electromagnet, a second electromagnet, and a third electromagnet according to an embodiment of the disclosure.

FIG. 12 illustrates a direct current (DC)-alternating current (AC) integrated magnetic field generated by a first electromagnet, a second electromagnet, and a third electromagnet according to an embodiment of the disclosure.

Referring to FIG. 12, each of the first to third electromagnets may integrally generate a direct current magnetic field (DC magnetic field) for driving the wired micro-robot and an alternating current magnetic field (AC magnetic field) for location recognition, and each magnetic field may be independently separated, so that the influence of interference on driving and location recognition is ignorable.

Figure 13:
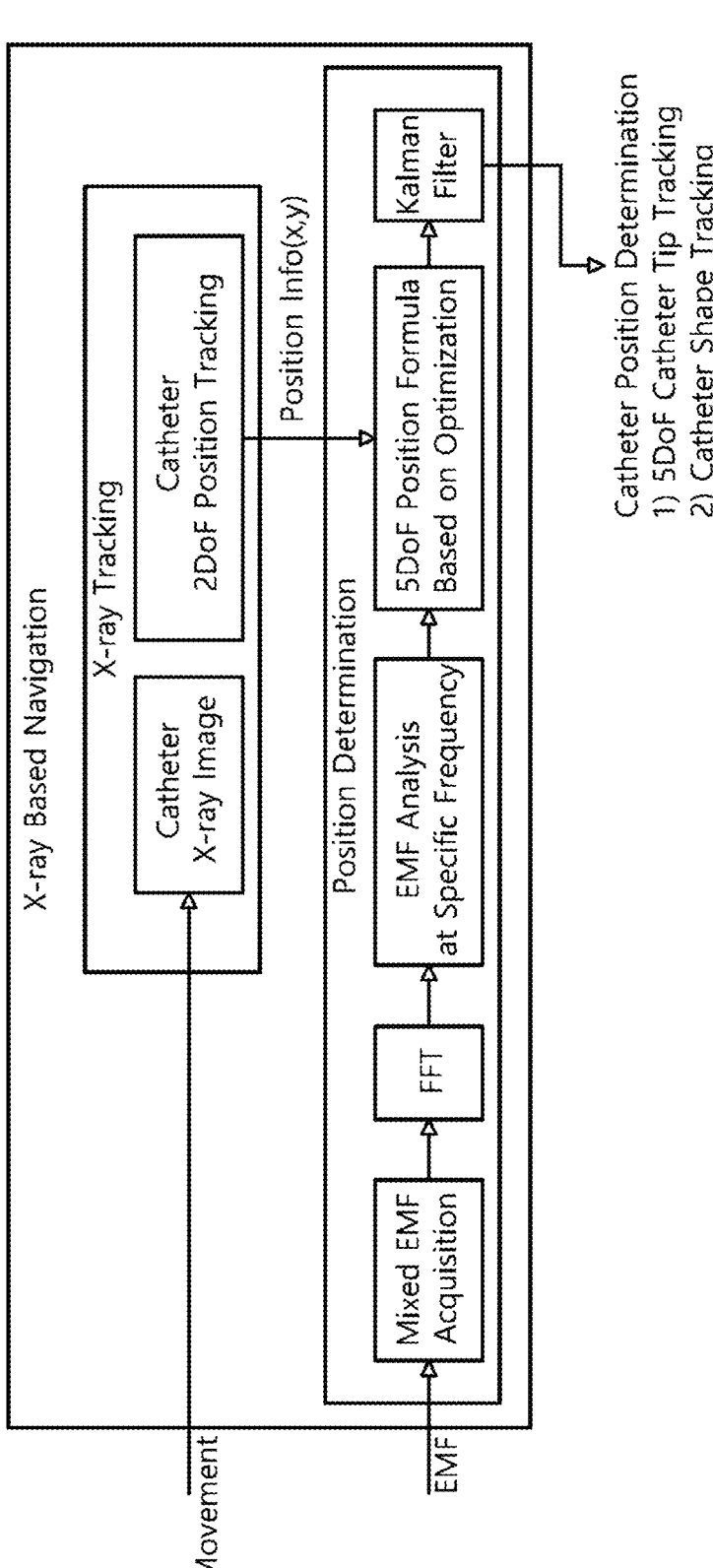
FIG. 13 is a flow chart illustrating location recognition of a micro-robot by using an electromotive force (EMF) induced through an alternating current (DC) magnetic field according to an embodiment of the disclosure.

FIG. 13 is a flow chart illustrating location recognition of a micro-robot by using an electromotive force (EMF) induced through an alternating current (DC) magnetic field according to an embodiment of the disclosure.

The detailed process of the location recognition operation (S400) of the micro-robot may be identified with reference to FIG. 13. The induced electromotive force (EMF) is induced in the form of mixed EMF in a single-axis Rx module through the AC magnetic fields of the first electromagnet 110, the second electromagnet 120(a), and the third electromagnet 120(b). The AC magnetic fields of the first electromagnet, second electromagnet, and third electromagnet have different specific frequencies and magnitudes, and these features appear in the form of mixed signals in the induced electromotive force of the Rx module 322, 324, 326. These mixed signals of electromotive force may be distinguished by frequency using Fast Fourier Transform (FFT) technology. That is, the location recognition operation (S400) includes first receiving a mixed signal generated from an Rx module included in the micro-robot by an AC magnetic field generated by applying an AC current to the first electromagnet, the second electromagnet, and the third electromagnet (S410), and then distinguishing and extracting a frequency-specific signal from the mixed signal (S420).

The second extraction operation (S430) may include extracting location estimation information of the Rx module from an X-ray image. The second extraction operation (S430) may be performed simultaneously with the mixed signal receiving operation (S410) or the first extraction operation (S420) or may be performed first or later.

The integration operation (S440) may be performed by integrating the frequency-specific signal with the location estimation information having two degrees of freedom (2DoF), thereby generating first location information.

The conversion operation (S450) may be performed by generating second location information having five degrees of freedom (5DoF) from the first location information. The three-dimensional location of the micro-robot may be recognized through second location information.

Specifically, the frequency-specific electromotive force signal generated in the first extraction operation (S420) may be integrated with the location estimation information having two degrees of freedom (2DoF; x, y location) of the micro-robot's distal end in the X-ray image plane through the X-ray device, be converted into location information by using 5DoF Inverse model, and pass through a Kalman filter for noise removal, thereby finally acquiring shape information (Catheter Bending Tracking) and micro-robot location information (Catheter Tip 5DoF Tracking) having five degrees of freedom.

The five-degree-of-freedom positioning formula may refer to determining the coordinates of one distal end of a robot having five degrees of freedom through an analysis by known forward kinematics and reverse kinematics. The Kalman filter may refer to a recursive filter that estimates the state of a linear dynamic system, based on measurements containing noise.

Figure 14:
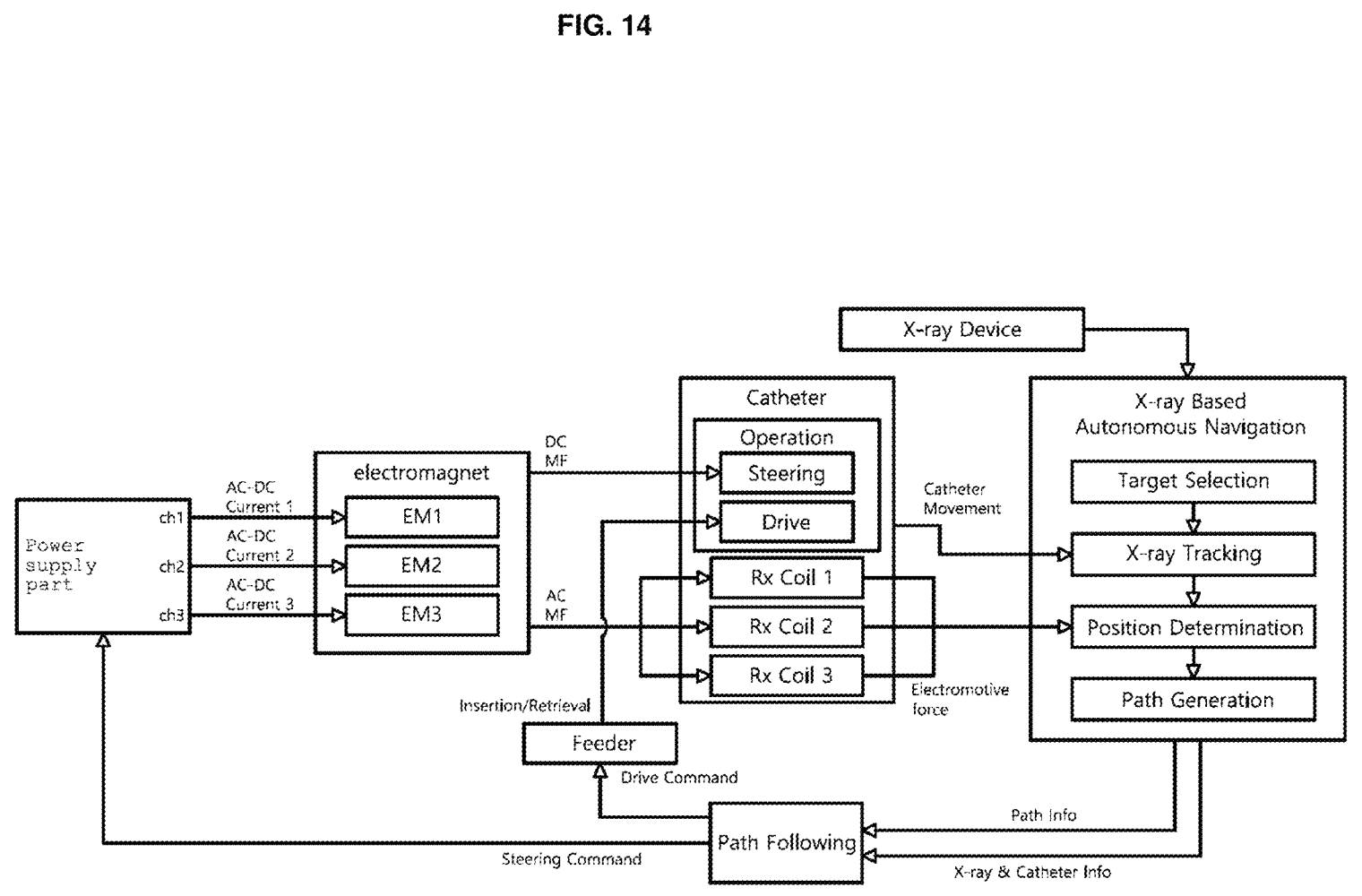

FIG. 14 is a flow chart illustrating a micro-robot autonomous targeting technology utilizing a micro-robot driving-location recognition synchronization technology according to an embodiment of the disclosure.

Referring to FIG. 14, the micro-robot autonomous targeting technology utilizing the micro-robot driving-location recognition synchronization technology may include a coordinate input operation (S1100) of receiving coordinates of a target lesion, a target lesion information generation operation (S1200) of generating location information of the lesion by using the coordinates of the target lesion; a path generation operation (S1300) of generating, by using the location information of the lesion, a movement path through which the micro-robot moves from the current location to the target lesion; and a micro-robot driving and location recognition operation (S1400) of driving the micro-robot according to the movement path and recognizing the location of the micro-robot in real time.

This micro-robot autonomous targeting technology may be executable by a computer program or software recorded in a computer-readable recording medium. In the micro-robot autonomous targeting technology, the coordinate input operation may be performed by a user using a haptic device, and the target lesion information generation operation, the path generation operation, and the micro-robot driving and location recognition operation may be performed by at least one processor implemented to execute a computer-readable command.

The coordinate input operation (S1100) may include receiving input of the coordinates of the target lesion. Specifically, the coordinate input operation may refer to selecting and input, by a user, the 3D coordinates of the target lesion within the X-ray-based autonomous image navigation system 1200 for the autonomous targeting function (target selection).

The target lesion information generation operation (S1200) may include generating location information of the lesion by using the coordinates of the target lesion.

The path generation operation (S1300) may include generating, by using the location information of the lesion, a movement path through which the micro-robot moves from the current location to the target lesion. That is, a process of generating a targeting path by integrating the generated location information of the target lesion and the location information of the micro-robot may be further implemented.

Finally, the micro-robot driving and location recognition operation (S1400) may include driving the micro-robot according to the movement path and recognizing the location of the micro-robot in real time, and specifically, may be performed while showing the same flow as described in FIG. 11. In addition, a control method (path-following) enabling follow of the targeting path through the real-time location of the micro-robot, based on the targeting path may be implemented. This may be performed by calculating the next movement of the micro-robot in advance by following the targeting path in real time (path-following) to transmit a required command (driving command & steering command) to the power supply part and the feeder.

An apparatus for implementing the method of synchronizing the driving and location recognition of a micro-robot and the micro-robot autonomous targeting method using the same is optimal when the apparatus includes three electromagnets, which are the first electromagnet, the second electromagnet, and the third electromagnet, as described above, in terms of the size of the entire apparatus, the drive performance of the micro-robot, and the compatibility with an X-ray device.

The disclosure described above is not limited to the above-described embodiments and the attached drawings, as various substitutions, modifications, and changes may be made without departing from the technical spirit of the disclosure by an ordinary skilled person in the art to which the disclosure pertains.

DESCRIPTIONS OF SYMBOLS

100: Electromagnet module 110: First electromagnet
111: First support plate 112: Second support plate 113: First winding 114: Center part
115: Connection part
120(*a*): Second electromagnet 120(*b*): Third electromagnet
121: Upper side surface 122: Lower side surface
123: Second winding, third winding 125: Core part
200: Bed 210: Support part
220: Bent part
300: Micro-robot 310: Robot body
322: First Rx coil 324: Second Rx coil
326: Third Rx coil
1000: Bed-integrated electromagnetic field apparatus 1100: X-ray device
1200: Image navigation system 1300: Catheter insertion-retrieval apparatus
1500: Micro-robot guidance apparatus
S100: Image acquisition operation S200: Current application operation
S300: Steering operation S400: Location recognition operation
S410: Mixed signal receiving operation S420: First extraction operation
S430: Second extraction operation S440: Integration operation
S450: Conversion operation
S1100: Coordinate input operation
S1200: Target lesion information generation operation
S1300: Path generation operation
S1400: Micro-robot driving and location recognition operation

INDUSTRIAL APPLICABILITY

The inventors have manufactured a bed-integrated electromagnetic field apparatus including a bed, a first electromagnet arranged in the bed, and second and third electromagnets arranged to form a predetermined angle with the first electromagnet, and have confirmed that the movement control and location recognition of a micro-robot may be performed simultaneously using the apparatus, and further, that when only the coordinates of a target lesion are input by a user, the micro-robot may be accurately targeted to the lesion site autonomously through location recognition information of the micro-robot acquired in real time and micro-robot drive utilizing the information.

Accordingly, the disclosure is to provide a method of synchronizing driving and location recognition of a micro-robot.

Also, the disclosure is to provide a micro-robot autonomous targeting method.

Also, the disclosure is to provide a computer program recorded in a computer-readable recording medium for executing a micro-robot autonomous targeting method.

Also, the disclosure is to provide a micro-robot autonomous targeting system including at least one processor for executing a micro-robot autonomous targeting method.

What is claimed is:
1. A method of synchronizing driving and location recognition of a micro-robot, the method comprising:
   an image acquisition operation of acquiring an X-ray image of an Rx module by using an X-ray device;
   a current application operation of independently applying a direct current-alternating current (DC-AC) integrated current to each of a first electromagnet, a second electromagnet, and a third electromagnet included in an electromagnetic field apparatus;

a steering operation of driving a micro-robot by applying a DC current to the first electromagnet, the second electromagnet, and the third electromagnet; and a location recognition operation of recognizing location of the micro-robot by using an AC magnetic field generated by applying an AC current to the first electromagnet, the second electromagnet, and the third electromagnet, wherein the location recognition operation comprises:

a mixed signal reception operation of receiving a mixed signal generated from the Rx module included in the micro-robot by the AC magnetic field generated by applying the AC current to the first electromagnet, the second electromagnet, and the third electromagnet;

a first extraction operation of distinguishing and extracting a frequency-specific signal from the mixed signal;

a second extraction operation of extracting location estimation information of the Rx module from the X-ray image;

an integration operation of integrating the frequency-specific signal with the location estimation information having two degrees of freedom (2DoF), thereby generating first location information; and a conversion operation of generating second location information having five degrees of freedom (5DoF) from the first location information.

2. The method of claim 1, wherein the electromagnetic field apparatus comprises:

the first electromagnet comprising a first support plate disposed on one side thereof, a second support plate disposed opposite to the first support plate, a center part configured to connect the first support plate and the second support plate through a connection part, and a first winding wound along a periphery of the center part;

the second electromagnet comprising a first core part comprising a first lower side surface disposed to configure a predetermined angle with the first electromagnet and a first upper side surface disposed opposite to the first lower side surface, and a second winding wound between the first lower side surface and the first upper side surface;

the third electromagnet comprising a second core part comprising a second lower side surface disposed to configure a predetermined angle with the first electromagnet and a second upper side surface disposed opposite to the second lower side surface, and a third winding wound between the second lower side surface and the second upper side surface; and a bed comprising one or more bent parts and a support part disposed between the one or more bent parts, the bed having the first electromagnet, the second electromagnet, and the third electromagnet arranged therein.

3. The method of claim 1, wherein the first extraction operation is performed using a Fast Fourier Transform (FFT) algorithm.

4. The method of claim 1, wherein the second extraction operation comprises extracting the location estimation information of the Rx module from the X-ray image by labeling coordinates at which the Rx module is estimated to be located.

5. The method of claim 1, wherein the integration operation is performed by transmitting x, y coordinate information of the Rx module from the X-ray image to a 5DoF model.

6. The method of claim 5, wherein the conversion operation is performed using the 5DoF model.

7. The method of claim 1, wherein the conversion operation further comprises a noise removal operation, and wherein the noise removal operation comprises removing noise from the second location information by using a Kalman filter.

* * * * *